US009913781B2

(12) United States Patent
Morioka et al.

(10) Patent No.: US 9,913,781 B2
(45) Date of Patent: Mar. 13, 2018

(54) DETERGENT COMPOSITION COMPRISING POLYVINYL ALCOHOL-CONTAINING PIGMENT GRANULES

(71) Applicant: KAO CORPORATION, Tokyo (JP)

(72) Inventors: Misako Morioka, Koto-ku (JP); Tatsuya Horibata, Wakayama (JP); Tatsuki Matsumoto, Wakayama (JP)

(73) Assignee: KAO CORPORATION, Tokyo (JP)

( * ) Notice: Subject to any disclaimer, the term of this patent is extended or adjusted under 35 U.S.C. 154(b) by 112 days.

(21) Appl. No.: 14/897,502

(22) PCT Filed: Jun. 4, 2014

(86) PCT No.: PCT/JP2014/064885
§ 371 (c)(1),
(2) Date: Dec. 10, 2015

(87) PCT Pub. No.: WO2014/199884
PCT Pub. Date: Dec. 18, 2014

(65) Prior Publication Data
US 2016/0120768 A1    May 5, 2016

(30) Foreign Application Priority Data

Jun. 13, 2013 (JP) ................................. 2013-124623

(51) Int. Cl.
| A61K 8/02 | (2006.01) |
| A61Q 5/02 | (2006.01) |
| A61Q 19/10 | (2006.01) |
| C11D 3/40 | (2006.01) |
| A61K 8/81 | (2006.01) |
| A61K 8/19 | (2006.01) |
| C11D 3/37 | (2006.01) |
| A61K 8/42 | (2006.01) |
| A61K 8/34 | (2006.01) |
| A61K 8/49 | (2006.01) |

(52) U.S. Cl.
CPC .......... *A61K 8/0225* (2013.01); *A61K 8/0275* (2013.01); *A61K 8/19* (2013.01); *A61K 8/34* (2013.01); *A61K 8/345* (2013.01); *A61K 8/42* (2013.01); *A61K 8/494* (2013.01); *A61K 8/8129* (2013.01); *A61K 8/8176* (2013.01); *A61K 8/8182* (2013.01); *A61Q 5/02* (2013.01); *A61Q 19/10* (2013.01); *C11D 3/3753* (2013.01); *C11D 3/3776* (2013.01); *C11D 3/40* (2013.01); *A61K 2800/41* (2013.01); *A61K 2800/43* (2013.01)

(58) Field of Classification Search
CPC ....... C11D 3/40; C11D 3/3753; C11D 3/3776; A61Q 5/02; A61Q 19/10; A61K 8/0225; A61K 8/8129; A61K 8/8176; A61K 8/19; A61K 8/42; A61K 8/34; A61K 8/345; A61K 8/494; A61K 8/8182; A61K 8/0275; A61K 2800/43; A61K 2800/41
See application file for complete search history.

(56) References Cited

U.S. PATENT DOCUMENTS

| 4,255,375 A * | 3/1981 | Macpherson ....... C09B 67/0017 106/262 |
| 4,264,552 A * | 4/1981 | McMahon ................. B01J 2/16 264/117 |
| 4,277,288 A * | 7/1981 | Lawrence .................. B01J 2/16 106/413 |
| 6,288,142 B1 * | 9/2001 | Bugnon ................... C08K 9/08 428/407 |
| 6,663,960 B1 * | 12/2003 | Murakami ............. C09K 11/02 162/140 |
| 2003/0049447 A1 | 3/2003 | Perrier et al. |
| 2005/0069704 A1 * | 3/2005 | Rathschlag .......... C09B 67/0004 428/402.21 |
| 2006/0058206 A1 | 3/2006 | Walls et al. |
| 2008/0069981 A1 * | 3/2008 | Ming ....................... B41M 5/52 428/32.34 |
| 2012/0178662 A1 | 7/2012 | Lachmann et al. |
| 2012/0183479 A1 | 7/2012 | Loeffler et al. |
| 2013/0172473 A1 * | 7/2013 | Rathschlag ........... C09C 1/0024 524/513 |

FOREIGN PATENT DOCUMENTS

| CN | 1616554 A | 5/2005 |
| EP | 1 518 903 A1 | 3/2005 |

(Continued)

OTHER PUBLICATIONS

International Search Report dated Aug. 26, 2014, for PCT/JP2014/064885 Filed Jun. 4, 2014.

(Continued)

*Primary Examiner* — Charles Boyer
(74) *Attorney, Agent, or Firm* — Oblon, McClelland, Maier & Neustadt, L.L.P.

(57) ABSTRACT

The present invention relates to [1] a detergent composition including pigment granules containing (A) from 10 to 95% by mass of a water-insoluble pigment, and (B) at least two compounds selected from the group consisting of polyvinyl alcohol, a polyvinyl alcohol derivative, polyvinyl pyrrolidone and a polyvinyl pyrrolidone derivative; and [2] a process for producing the detergent composition according to the above [1], including the steps of mixing and granulating a powder containing the water-insoluble pigment (A) and a solution of the component (B) to obtain a granulated product; drying the resulting granulated product to obtain the pigment granules; and mixing the pigment granules with a detergent. The detergent composition is capable of not only can satisfying both of rich foaming and good preparation stability, but also exhibiting sufficient coloration of foams and readily controlling a coloring time of the foams without damage to motivation of the user to use the detergent, and therefore can provide a comfortable feeling of use and a suitable configuration of use according to the applications by the user.

11 Claims, No Drawings

(56) References Cited

FOREIGN PATENT DOCUMENTS

| JP | 2002-363436 A | 12/2002 |
|---|---|---|
| JP | 2008-31187 A | 2/2008 |
| JP | 2012-533637 A | 12/2012 |
| TW | 200817042 A | 4/2008 |

OTHER PUBLICATIONS

Extended European Search Report dated Jan. 4, 2017 in Patent Application No. 14811630.4.

* cited by examiner

US 9,913,781 B2

DETERGENT COMPOSITION COMPRISING POLYVINYL ALCOHOL-CONTAINING PIGMENT GRANULES

FIELD OF THE INVENTION

The present invention relates to a detergent composition, and more particularly, to a detergent composition capable of fully coloring foams formed upon use, and a process for producing the detergent composition.

BACKGROUND OF THE INVENTION

Detergents such as a body shampoo and a facial cleanser are usually used in a foamed state. The advantageous effects attained by using the detergents in a foamed state include (i) a wider washable rage even when the detergents are used in a small amount; (ii) an improved touch feeling at respective body portions to be washed; (iii) an enhanced feeling of use of the detergents upon washing by colored foams, and the like.

For the purpose of improving pleasure upon use and a feeing of use, a composition including pigment-containing granules and a composition capable of generating colored foams have conventionally been proposed.

For example, JP 2010-202615A (Patent Literature 1) discloses a solid soap that is colored from orange to red, and includes a fatty acid salt having 12 to 20 carbon atoms, glycerol, a chelate agent, an antioxidant and a petal extract, in which the glycerol, chelate agent and antioxidant are respectively used in a small amount, and the petal extract is used in an amount of from 0.001 to 10 parts by mass on the basis of 100 parts by mass of the fatty acid salt.

JP 2000-169338A (Patent Literature 2) discloses a cosmetic composition including collapsible granules having a specific particle size which are prepared by coating granules obtained by granulating water-insoluble primary particles having an average particle size of 50 μm or less using a water-soluble binder, with a water-insoluble coating agent.

JP 4-338314A (Patent Literature 3) discloses a cosmetic including granules having a double structure including an inner core and an outer layer which are different in color from each other, in which a powder constituting the inner core is a non-hydrophobic powder and a powder constituting the outer layer is a hydrophobic powder. The cosmetic is readily collapsed by massage operations or the like and rapidly undergoes color change to that of the inner core by which the user is notified of an end point of the massage operations.

JP 4-198116A (Patent Literature 4) discloses a scrubbing cleanser including a mixture of granules prepared by granulating a scrubbing fine powder having an average particle size of 20 μm or less and containing neither a sugar powder nor a sugar alcohol powder using a water-soluble binder, and detergent-containing powder or granules, which can notify the user of termination of the cleaning operation.

JP 11-263996A (Patent Literature 5) discloses a detergent including a pigment in such an amount that the detergent generates colored foams when foamed, and the foams are decolorized when washed away with water, so as to visually enjoy a color of the foams.

JP 2012-533637A (Patent Literature 6) discloses a detergent composition including microencapsulated colorant granules constituted of a core containing a colorant, a cellulose and a polyol, and a shell containing a specific polymer, in which the microcapsule is gradually collapsed by physical stimulus such as scrubbing upon use of the detergent to notify the user of a cleaning time by change in color of foams.

SUMMARY OF THE INVENTION

The present invention relates to the following aspects [1] and [2].

[1] A detergent composition including pigment granules containing (A) from 10 to 95% by mass of a water-insoluble pigment, and (B) at least two compounds selected from the group consisting of polyvinyl alcohol, a polyvinyl alcohol derivative, polyvinyl pyrrolidone and a polyvinyl pyrrolidone derivative.

[2] A process for producing the detergent composition according to the above aspect [1] including the steps of mixing and granulating a powder containing the water-insoluble pigment (A) and a solution of the component (B) to obtain a granulated product; drying the resulting granulated product to obtain the pigment granules; and mixing the pigment granules with a detergent.

DETAILED DESCRIPTION OF THE INVENTION

The soap described in Patent Literature 1 is formed by previously tinting a preparation (bulk) into a deep color with an aqueous plant extract for the purpose of generating colored foams, so that the color of the preparation is reflected on the resulting foams even after the soap is diluted or foamed. Thus, in Patent Literature 1, no granules containing a water-insoluble pigment are used.

The cosmetic composition described in Patent Literature 2 undergoes the change in color of the granules upon massage operations to notify the user of application of the cosmetic composition to skin and a degree of the massage operations. Therefore, the color of the granules in the cosmetic composition is not reflected even on a color of foams generated upon dilution and foaming thereof.

The cosmetic and detergent described in Patent Literatures 3 and 4 aim at providing a measure for a use time thereof, and include granules that are tinted into a deep color with a water-insoluble pigment such that the user is notified of termination of washing by following the change in color of the granules upon use.

In Patent Literature 5, the colored foams are generated by increasing the amount of a synthetic pigment or a colored medicinal extract compounded in the detergent to a specific range. However, the preparation (bulk) is deeply colored by increasing the amount of the pigment used therein. For this reason, in Patent Literature 5, there is described such an embodiment that the preparation is filled in an aerosol container or a pump foam container to inject the colored foams therefrom, and the pigment concretely used therein is a water-soluble pigment.

In Patent Literature 6, the shell portion is collapsed by physical stimulus such as scrubbing to expose the core portion outside, thereby generating the colored foams. However, in the hand-washing test concretely described in Patent Literature 6, the time required until generating the colored foams is as long as about 2 min.

Detergents are usually diluted and foamed upon use. However, since a liquid film of the respective foams is very thin, the foams generally have a white appearance owing to total reflection or irregular reflection of light thereon. For this reason, in order to fully color the foams, it is necessary to strongly color the detergents themselves. As a result, the liquid color of the detergents becomes excessively deep, so that it may be difficult to motivate the user to use the detergents. On the other hand, if the amount of a colorant added to the detergents is merely increased, there tends to occur such a problem that the resulting preparation is deteriorated in stability or foamability. In addition, although the water-soluble pigment is capable of more readily coloring the detergents even when used in a small amount, there tends to occur such a problem that the color of the pigment oozed is transferred into the preparation (bulk) and the skin of the user is undesirably colored therewith.

The compositions for forming colored foams as described in Patent Literatures 1 and 5 both are improved in properties thereof to a certain extent, but fail to attain good foamability, good stability, sufficient coloration of foams and good bulk appearance sufficient to motivate the user to use these products. Whereas, Patent Literatures 2 to 4 are concerned with coloration of the granules, and therefore the preparation (bulk) and coloration of the foams are not taken into consideration therein.

The detergent composition described in Patent Literature 6 is improved in bulk appearance by microencapsulating the pigment. However, in order to obtain fully colored foams, it is necessary to apply a strong physical stimulus to the microcapsule for a long period of time, so that large psychological or physical burden tends to be imposed on the user. In addition, in Patent Literature 6, there is described no concrete method of controlling collapsibility of the microcapsule. For example, in the method of controlling a thickness of the shell portion, the collapsibility of the granules by physical stimulus upon production and filling is increased or decreased in association with the collapsibility of the granules by scrubbing upon use. For this reason, it is not possible to satisfy both of good stability of the granules upon production and filling and good collapsibility of the granules by scrubbing at the same time.

In consequence, the present invention relates to an excellent detergent composition that is capable of not only satisfying both of rich foaming and preparation stability, but also exhibiting sufficient colorability for foams without any damage to motivation of the user to use the detergent, and can be readily controlled in coloring time of foams to thereby provide a comfortable feeling of use and a suitable use configuration thereof according to applications by the user; and a process for producing the detergent composition.

The present inventors have found that the above conventional problems can be solved by the detergent composition including pigment granules that have a water-insoluble pigment content of from 10 to 95% by mass and contain at least two compounds selected from the group consisting of polyvinyl alcohol, a polyvinyl alcohol derivative, polyvinyl pyrrolidone and a polyvinyl pyrrolidone derivative.

The present invention relates to the following aspects [1] and [2].

[1] A detergent composition including pigment granules containing (A) from 10 to 95% by mass of a water-insoluble pigment, and (B) at least two compounds selected from the group consisting of polyvinyl alcohol, a polyvinyl alcohol derivative, polyvinyl pyrrolidone and a polyvinyl pyrrolidone derivative.

[2] A process for producing the detergent composition according to the aspect [1], including the steps of mixing and granulating a powder containing the water-insoluble pigment (A) and a solution of the component (B) to obtain a granulated product; drying the resulting granulated product to obtain the pigment granules; and mixing the pigment granules with a detergent.

According to the present invention, there are provided an excellent detergent composition that is capable of not only satisfying both of rich foaming and preparation stability, but also suppressing coloration of a preparation (bulk) and exhibiting sufficient colorability for foams without any damage to motivation of the user to use the detergent, and can be readily controlled in coloring time of foams to thereby provide a comfortable feeling of use and a suitable use configuration thereof according to applications by the user; and a process for producing the detergent composition.

[Detergent Composition]

The detergent composition of the present invention includes pigment granules containing (A) from 10 to 95% by mass of a water-insoluble pigment, and (B) at least two compounds selected from the group consisting of polyvinyl alcohol, a polyvinyl alcohol derivative, polyvinyl pyrrolidone and a polyvinyl pyrrolidone derivative. The detergent composition is capable of generating colored foams upon use.

In the following, the respective components and production process used in the present invention are described.

[Pigment Granules]

The pigment granules used in the present invention (hereinafter also referred to merely as "granules") contain the water-insoluble pigment (A) in an amount of from 10 to 95% by mass, from the viewpoint of sufficient coloration of foams and preparation stability, and preferably further contain the component (B), if required together with a powder, etc., from the viewpoint of well controlling the coloration of foams.

<Water-Insoluble Pigment (A)>

The water-insoluble pigment (A) (hereinafter also referred to merely as a "pigment") used in the present invention is not particularly limited as long as it can be generally used in detergents, cosmetics, etc. The term "water-insoluble" pigment as used herein means that the amount of the pigment dissolved in 100 g of water at 20° C. is preferably not more than 1 g, and more preferably not more than 0.1 g.

Also, in the present specification, the term "pigment" as used herein means a component capable of developing a color of the detergent upon use when it is compounded in the pigment granules, and is not particularly limited merely to so-called pigments.

The water-insoluble pigment used in the present invention may be an optional pigment selected from synthetic or natural, inorganic or organic pigments.

Specific examples of the water-insoluble inorganic pigments include tourmaline, chromium oxide, yellow iron sesquioxide, black iron oxide, red iron oxide, cobalt oxide, ultramarine blue, chromium hydroxide, titanium oxide, zinc oxide, talc and manganese violet.

Specific examples of the water-insoluble organic pigments include azo-based pigments such as azo lake pigments, insoluble azo pigments and condensed azo pigments, phthalocyanine-based pigments such as phthalocyanine blue and phthalocyanine green, quinacridone, isoindolinone and dioxazine.

These pigments may be used alone or in combination of any two or more thereof.

The water-insoluble pigment is preferably in the form of an organic pigment, from the viewpoint of sufficient coloration of foams Specific examples of the organic pigment include lycopene, carotene, xanthophyll, chlorophyll, Helindone Pink (Red #226), lake red (Red #203 and #204), lithol red, permanent orange, phthalocyanine blue and Hansa yellow.

The content of the water-insoluble pigment (A) in the pigment granules is from 10 to 95% by mass, from the viewpoints of color of an appearance of the bulk, preparation stability, foamability upon washing and coloration of foams.

From the aforementioned viewpoints, the content of the water-insoluble pigment (A) in the pigment granules is preferably not less than 12% by mass, more preferably not less than 15% by mass, and even more preferably not less than 18% by mass. The upper limit of the content of the water-insoluble pigment (A) in the pigment granules is preferably not more than 90% by mass, more preferably not more than 85% by mass, and even more preferably not more than 80% by mass. Specifically, the content of the water-insoluble pigment (A) in the pigment granules is preferably from 12 to 90% by mass, more preferably from 15 to 85% by mass, and even more preferably from 18 to 80% by mass.

<Powder>

The pigment granules used in the present invention preferably contain a water-insoluble powder, for the viewpoints of collapsibility of the granules upon washing, controllability of a hardness of the granules, stability, dispersing effect of the pigment in the preparation, appearance of the granules and coloration of foams upon washing.

The term "water-insoluble" powder as used herein means that the solubility of the powder as measured by dissolving 1 part by mass of the powder to be measured in 99 parts by mass of water at 25° C. is less than 50% by mass. Meanwhile, the solubility of the powder is calculated from an amount of solids in a filtrate obtained by subjecting an aqueous solution of the powder to filtration using a filter paper (No. 2).

As the water-insoluble powder, there may be mentioned an inorganic powder and an organic powder.

Examples of the water-insoluble inorganic powder include talc, mica, kaolin, bentonite, sericite, sepiolite, silica, calcium carbonate, calcium oxide, magnesium oxide, titanium dioxide-coated mica, titanium oxide, aluminum oxide, silicic acid anhydride and hydroxy calcium apatite, as well as mother-of-pearl substances.

Examples of the water-insoluble organic powder include (i) powders formed of fine particles of synthetic polymers including polyethylene, polypropylene, polyamides, polyethylene terephthalate, polystyrene, polyurethane and crosslinked products thereof; sodium poly(meth)acrylate, poly (meth)acrylic acid esters and crosslinked products thereof, and rubbers such as ethylene rubbers, propylene rubbers, styrene-butadiene rubbers, butadiene rubbers and silicone rubbers, and crosslinked products thereof, and (ii) powders formed of natural polymers or derivatives thereof including celluloses and derivatives thereof, chitosan and derivatives thereof, starches such as corn starch, fruit shells, fatty acids, plant extract powders, enzymes, cyclodextrin, silk powders, metal soaps, sodium hyaluronate, vitamin C, and dipotassium glycyrrhizinate.

These powders may be used alone or in combination of any two or more thereof.

Of these powders, preferred are inorganic powders such as talc, mica, kaolin, bentonite, sericite, magnesium oxide, calcium oxide, titanium dioxide-coated mica, titanium oxide and aluminum oxide; and organic powders such as polyethylene, polypropylene, crystalline celluloses, modified celluloses, corn starch, starches, fatty acids, plant extract powders, enzymes, cyclodextrin, silk powders, metal soaps, sodium hyaluronate, vitamin C and dipotassium glycyrrhizinate.

The shape of the powder is not particularly limited, and may be any of a spherical shape, a generally spherical shape, a flat plate shape, a bar shape and a deformed shape obtained by pulverization or the like. The powder may also be in the form of hollow particles, porous particles, etc.

The average particle size of the powder is preferably not less than 5 μm and more preferably not less than 10 μm, and is also preferably not more than 70 μm and more preferably not more than 60 μm, from the viewpoints of facilitated granulation, less uncomfortable feeling upon collapse of particles of the powder and good washing-out property.

The content of the powder in the pigment granules is preferably in the range of from 0 to 80% by mass. Specifically, the content of the powder in the pigment granules is preferably not more than 75% by mass, more preferably not more than 70% by mass, and even more preferably not more than 50% by mass, from the viewpoints of good stability and granulation property of the granules in the detergent, and is also preferably not less than 10% by mass, more preferably not less than 20% by mass, and even more preferably not less than 30% by mass, from the viewpoint of uniform dispersion of the pigment in the granules upon granulation.

The mass ratio of the pigment to the powder (pigment/powder) is preferably not less than 0.1, more preferably not less than 0.15, and even more preferably not less than 0.2, and is also preferably not more than 6, more preferably not more than 4, and even more preferably not more than 2.5.

<Component (B)>

The at least two compounds selected from the group consisting of polyvinyl alcohol, a polyvinyl alcohol derivative, polyvinyl pyrrolidone and a polyvinyl pyrrolidone derivative which are used as the component (B) in the present invention may be, in general, frequently used as a binder.

The component (B) is incorporated in the pigment granules used in the present invention from the viewpoints of granulation and formation of the granules, retention of stability of the granules, impartment of adequate collapsibility of the granules upon using the detergent, etc.

By using the component (B) in the pigment granules, it is possible to satisfy both of preparation stability of the bulk and coloration of foams, and control and impart suitable properties according to dosage forms or use conditions of the detergent.

The content of the component (B) in the pigment granules is preferably not less than 0.05% by mass, more preferably not less than 0.1% by mass, and even more preferably not less than 0.5% by mass, from the viewpoints of good stability and granulation property of the granules in the detergent, and is also preferably not more than 50% by mass, more preferably not more than 30% by mass, and even more preferably not more than 15% by mass, from the viewpoints of uniform diffusion of the pigment in the pigment granules upon use.

In addition, known binders such as ethyl cellulose, hydroxypropyl cellulose, acetyl cellulose, hydroxymethyl cellulose, methyl cellulose, carageenan, agar-agar, gelatin, alginic acid, alginic acid derivatives, gum arabic, shellac, sodium polyacrylate, polyacrylic acid derivatives, methacrylic acid derivatives and vinyl acetate may be optionally used in combination with the component (B) used in the present invention.

(Polyvinyl Alcohol)

The polyvinyl alcohol (PVA) as used in the present invention means a non-modified PVA. Examples of commercially available products of PVA used in the present invention include, but are not particularly limited to, "GOHSENOL" series (such as "GL-03", "EG-05", "EG-30", "EG-40", etc.) available from Nippon Synthetic Chemical Industry Co., Ltd., POVAL (PVA) series (such as "403", "405", "420", "420H", "424H", "203", "205", "210", "217", "220", "224", "235", "217E", "220E", "224E", etc.) available from Kuraray Co., Ltd., and the like.

The degree of saponification of PVA is preferably not less than 70%, more preferably not less than 75%, and even more preferably not less than 80%, from the viewpoint of good stability of the granules in the detergent composition, and is also preferably not more than 99%, and more preferably not more than 95%, from the viewpoint of good collapsibility of the granules upon use to obtain fully colored foams.

The average molecular weight of the polyvinyl alcohol is preferably not more than 200,000, more preferably not more than 180,000, and even more preferably not more than 150,000, from the viewpoint of easiness of handling. The average molecular weight of the polyvinyl alcohol may be calculated from the value determined by a viscosity measuring method according to a Stauginger's viscosity formula.

(Polyvinyl Alcohol Derivative)

As the polyvinyl alcohol (PVA) derivative, there may be used at least one compound selected from the group consisting of anion-modified PVA derivatives such as a carboxylic acid-modified PVA, an undecylenic acid-modified PVA and a sulfonic acid-modified PVA; cation-modified PVA derivatives such as an ammonium-modified PVA, a sulfonium-modified PVA and an amino group-modified PVA; and the like.

Examples of commercially available products of the PVA derivative used in the present invention include, but are not particularly limited to, "GOHSENEX T" series (such as "T-350", "T-330", etc.), "GOHSENEX L" series (such as "L-3266", etc.) and "GOHSENEX K" series (such as "K-434", etc.) all available from Nippon Synthetic Chemical Industry Co., Ltd.; and "K Polymer" series (such as "KL-506", "KL-318", "KL-118", "KM-618", "KM-118", etc.) and "C Polymer" series (such as "C-506", "CM-318", etc.) all available from Kuraray Co., Ltd. Of these PVA derivatives, from the viewpoint of good stability when compounded in the detergent composition, preferred are anion-modified PVA derivatives, and more preferred at least one compound selected from the group consisting of a carboxylic acid-modified PVA and a sulfonic acid-modified PVA.

The degree of saponification of the PVA derivative is preferably not less than 70%, more preferably not less than 75%, and even more preferably not less than 80%, from the viewpoint of good stability of the granules in the detergent, and is also preferably not more than 99.5%, and more preferably not more than 99%, from the viewpoint of good collapsibility of the granules upon use to obtain fully colored foams.

The anion-modified PVA derivatives may be produced as follow. For example, the carboxylic acid-modified PVA may be produced by introducing a carboxy group-containing compound into the polyvinyl alcohol by conventionally known methods. Examples of the carboxy group-containing compound include fumaric acid, maleic acid, itaconic acid, maleic anhydride, phthalic anhydride, trimellitic anhydride, acrylic acid, and salts of these compounds. Also, the sulfonic acid-modified PVA may be produced by introducing a sulfonic group-containing compound into the polyvinyl alcohol by conventionally known methods. Examples of the sulfonic group-containing compound include ethylenesulfonic acid, allylsulfonic acid, methallylsulfonic acid, 2-acrylamide-2-methylpropane sulfonic acid, p-sulfonic acid benzaldehyde, and salts of these compounds.

Of these anion-modified PVA derivatives, particularly preferred is the maleic acid-modified PVA.

The degree of acid modification of the anion-modified PVA derivatives is preferably not less than 0.5 mol %, and more preferably not less than 1 mol %, from the viewpoints of rapid collapse of the granules upon use and improvement in coloration of foams, and is also preferably not more than 10 mol %, and more preferably not more than 5 mol %, from the viewpoint of good stability of the granules in the detergent.

The average molecular weight of the polyvinyl alcohol derivative is preferably not more than 200,000, more preferably not more than 180,000, and even more preferably not more than 150,000, from the viewpoint of easiness of handling. The average molecular weight of the polyvinyl alcohol derivative may be calculated from the value determined by a viscosity measuring method according to a Stauginger's viscosity formula.

(Polyvinyl Pyrrolidone and Polyvinyl Pyrrolidone Derivative)

As the polyvinyl pyrrolidone (PVP) and the polyvinyl pyrrolidone derivative, there may be mentioned at least one compound selected from the group consisting of polyvinyl pyrrolidone itself and copolymers of polyvinyl pyrrolidone with acrylic acid, methacrylic acid, vinyl alcohol, etc. Examples of commercially available products of the polyvinyl pyrrolidone (PVP) and the polyvinyl pyrrolidone derivative used in the present invention include, but are not particularly limited to, "LUVISKOL" series (such as "K17", "K30", "K90", "VA73E", "VA64P", "VA37E", etc.) available from BASF, PVP series (such as "K-15", "K-30", "K-90", "K-15W", "K-30W", etc.) available from ISP, and the like. Of these compounds, from the viewpoints of good handing property, facilitated collapse of the granules upon use, and sufficient coloration of foams, polyvinyl pyrrolidone is preferably used.

As the component (B), there are used at least two compounds selected from the group consisting of the polyvinyl alcohol, the polyvinyl alcohol derivative, the polyvinyl pyrrolidone and the polyvinyl pyrrolidone derivative. Among these compounds, from the viewpoints of good stability of the granules in the detergent and good granulation property of the granules, the component (B) preferably contains (b1) at least one compound selected from the group consisting of the polyvinyl alcohol and the polyvinyl alcohol derivative which preferably have a viscosity of not less than 15 mPa·s, more preferably not less than 18 mPa·s, and even more preferably not less than 20 mPa·s as measured at 20° C. with respect to a 4% aqueous solution thereof using a B-type viscometer. In addition, from the viewpoint of uniform diffusion of the pigment in the pigment granules upon use, the component (B) preferably contains (b2) at least one compound selected from the group consisting of the polyvinyl alcohol and the polyvinyl pyrrolidone which preferably have a viscosity of less than 15 mPa·s, more preferably less than 13 mPa·s, and even more preferably less than 11 mPa·s as measured at 20° C. with respect to a 4% aqueous solution thereof.

Further, from the viewpoints of good stability of the granules in the detergent composition and efficient control of collapsibility of the granules upon use, the combination of the at least one compound (b1) selected from the group consisting of the aforementioned polyvinyl alcohol and polyvinyl alcohol derivative and the at least one compound (b2) selected from the group consisting of the aforementioned polyvinyl alcohol and polyvinyl pyrrolidone is preferably used. Specific examples of the preferred combination of the compounds (b1) and (b2) include the combination of the aforementioned polyvinyl alcohol derivative (b1) and the aforementioned polyvinyl alcohol (b2), the combination of the aforementioned polyvinyl alcohol derivative (b1) and the aforementioned polyvinyl pyrrolidone (b2), and the combination of the aforementioned polyvinyl alcohol (b1) and the aforementioned polyvinyl pyrrolidone (b2).

From the viewpoints of good stability of the pigment granules in the detergent and efficient control of collapsibility of the granules upon use, the compounding mass ratio of the compound (b1) to the compound (b2) [(b1)/(b2)] is preferably not less than 0.05, more preferably not less than 0.1, and even more preferably not less than 0.15, and is also preferably not more than 3.0, more preferably not more than 2.5, and even more preferably not more than 2.0. Specifically, the compounding mass ratio [(b1)/(b2)] is preferably in the range of from 0.05 to 3.0, more preferably from 0.1 to 2.5, and even more preferably from 0.15 to 2.0.

(Alcohol (C))

The pigment granules used in the present invention contain the water-insoluble pigment (A) and the component (B), and may further contain an alcohol (C). However, when the content of the alcohol (C) in the pigment granules is excessively large, the pigment granules tend to be deteriorated in granulation property, so that remarkable coloration of the preparation bulk tends to be recognized. Therefore, the content of the alcohol (C) in the pigment granules is preferably not more than 5% by mass, more preferably not more than 4% by mass, even more preferably not more than 3% by mass, and further even more preferably not more than 2% by mass.

The alcohol (C) is an alcohol selected from the group consisting of ethanol and polyhydric alcohols. Specific examples of the alcohol (C) include ethanol (including synthetic ethanol and fermented alcohol), glycerol, propanediol, butylene glycol, dipropylene glycol, sorbitol, maltitol, xylitol and propylene glycol. Among these alcohols, the alcohols having a less influence even when incorporated into the pigment granules are glycerol, sorbitol, maltitol, xylitol, 1,3-butylene glycol and the like. Whereas, the alcohols having a large influence when incorporated into the pigment granules are ethanol, propylene glycol, dipropylene glycol and the like.

The alcohol (C) as used herein is intended to mean an alcohol to be added during the granulation step of the pigment granules, but exclude such an alcohol as oozed out of components of the detergent composition except for the pigment granules and infiltrated into the pigment granules upon preparing the detergent composition using the pigment granules subjected to the granulation and drying steps. This is because the pigment granules subjected to the granulation and drying steps are held in such a state that the component (B) is uniformly dispersed therein, so that the resulting granulated product is free from breakage of its structure even though the alcohol (C) contained in the detergent composition is thereafter infiltrated into the pigment granules.

(Other Components)

The pigment granules used in the present invention may also contain, in addition to the aforementioned components, optional components that may be used in ordinary detergent compositions, if required, unless the effects of the present invention are adversely affected. Examples of the optional components include surfactants, fatty acids, silicones, oils, extracts, antiseptic agents, humectants, polymers, amino acid derivatives, sugar derivatives, perfumes, drugs, etc.

<Production of Pigment Granules>

The pigment granules used in the present invention are collapsed by chemical stimulus and/or physical stimulus applied thereto upon using the detergent composition, so that the components in the granules such as the pigment are released therefrom. The chemical stimulus as used herein means the change in concentration of the pigment granules due to addition or evaporation of water, the change in pH under use conditions, the change in temperature, etc., whereas the physical stimulus as used herein means loads applied thereto upon foaming and coating, etc.

The method for producing the pigment granules is not particularly limited as long as the resulting pigment granules have the aforementioned properties, and includes various granulation methods such as rolling granulation, fluidized bed granulation, stirring granulation, extrusion granulation, spray-drying granulation, press (tableting) granulation, coating granulation and capsule granulation. Of these granulation methods, rolling granulation, fluidized bed granulation, stirring granulation, extrusion granulation and spray-drying granulation are preferably used for producing the pigment granules, because the components of the pigment granules are uniformly dispersed as a whole in the granules so that foams of the detergent are gradually and uniformly colored with less occurrence of color unevenness upon use.

<Configuration of Pigment Granules>

The shape of the pigment granules used in the present invention is not particularly limited, and may be any of a spherical shape, a generally spherical shape, a flat plate shape, a bar shape and a deformed shape obtained by pulverization or the like.

The average particle size of the pigment granules is not particularly limited. The average particle size of the pigment granules when compounded in the preparation is preferably not less than 20 μm, more preferably not less than 30 μm, and even more preferably not less than 50 μm, from the viewpoints of a thinned color of an appearance of the bulk, good stability of the preparation, and good foamability, and is also preferably not more than 1500 μm, more preferably not more than 900 μm, and even more preferably not more than 800 μm, from the viewpoint of less irritation to skin and uniform distribution of the granules upon use.

The average particle size of the pigment granules may be measured based on undersize mass distribution determined by a sieving method using a low-tap sieve shaker, etc.

[Detergent Composition]

The detergent composition of the present invention preferably contains the pigment granules containing from 10 to 95% by mass of the water-insoluble pigment (A) and the component (B), in an amount of not less than 0.001% by mass and not more than 5% by mass, from the viewpoint of sufficient coloration of foams upon use.

The content of the pigment granules in the detergent composition is preferably not less than 0.005% by mass, more preferably not less than 0.01% by mass, and even more preferably not less than 0.05% by mass, and the upper limit of the content of the pigment granules in the detergent composition is preferably not more than 4% by mass, more preferably not more than 2% by mass, and even more preferably not more than 1% by mass, from the viewpoint of good coloration of foams.

The concentration of the pigment in the detergent composition is preferably not less than 0.001% by mass, more preferably not less than 0.005% by mass, and even more preferably not less than 0.007% by mass, from the viewpoint of good coloration of foams, and is also preferably not more than 5% by mass, more preferably not more than 2% by mass, and even more preferably not more than 0.5% by mass, from the viewpoints of less risk of coloration of skin and thinned color of an appearance of the bulk.

(Electrical Conductivity)

The pigment granules used in the present invention is enhanced in collapsibility as the concentration of ions in water contained in the detergent composition is lowered. The enhancement in collapsibility of the pigment granules also tends to be exhibited even when the detergent composition is diluted with water in the manner similar to ordinary usage of detergent compositions. In general, detergents contain various ions derived from surfactants such as an ionic surfactant and a fatty acid soap, inorganic salts such as sodium chloride, salts contained as a by-product upon production of raw materials, etc., in a mixed state. Therefore, it may be difficult to estimate a concrete amount of ions in the water. However, by measuring an electrical conductivity of the water, it is possible to estimate an approximate ion titer in the water as a total relative amount thereof.

The measurement of the electrical conductivity of the detergent composition may be carried out by the following method irrespective of properties of the detergent composition. That is, 1 part by mass of the detergent composition is sampled, and 4 parts by mass of purified water is added thereto to prepare a uniform mixed solution or a viscous liquid as a sample solution, and then the electrical conductivity of the thus prepared sample solution is measured at 25° C. using a commercially available electrical conductivity meter (for example, "EC METER CM-60G" available from DKK-TOA Corporation).

The electrical conductivity of a 5-fold diluted solution of the detergent composition according to the present invention is preferably not less than 0.1 S/m, more preferably not less than 0.2 S/m, even more preferably not less than 0.3 S/m, and further even more preferably not less than 0.5 S/m, and is also preferably not more than 1.7 S/m, more preferably not more than 1.5 S/m, even more preferably not more than 1.0 S/m, and further even more preferably not more than 0.8 S/m, from the viewpoints of good stability upon production, filling and storage of the pigment granules as well as facilitated collapse of the granules upon use.

The "colored foams" as used herein mean that the change in color of foams of the detergent composition is visually recognized in comparison with the color of a detergent composition having the same composition except for compounding no pigment granules therein. When measured using an ordinary colorimeter in L*a*b* color specification system in which L*, a* and b* represent a lightness, a chromaticity in the red-green direction and a chromaticity in the yellow-blue direction, respectively, the change in color is more readily recognized as the color difference ΔE increases. Meanwhile, ΔE is represented by the following formula (1):

$$\Delta E=[(\Delta L^*)^2+(\Delta a^*)^2+(\Delta b^*)^2]^{1/2} \quad (1)$$

In the present invention, the color difference ΔE at which the colored foams are visually recognizable is preferably not less than 1, more preferably not less than 2, and even more preferably not less than 3. When ΔE is less than 1, it may be difficult to visually recognize the color of the colored foams and therefore determine whether or not the color of the colored foams is a sufficient chromatic color.

In addition, the expression "less coloration of the preparation (bulk)" or "thinned color of an appearance of the preparation (bulk)" means that the color difference (ΔE) of a stock solution (bulk) of the detergent composition is a significant difference in comparison with that of a detergent composition having the same composition except for compounding none of the aforementioned pigment granules therein. More specifically, the above color difference ΔE is preferably less than 30, more preferably less than 20, and even more preferably less than 12. When ΔE is not less than 30, the user tends to have a feeling of dislike or hesitation upon use thereof, so that there occurs such a risk that the motivation of the user to use the detergent composition is lost.

The pigment granules compounded in the detergent composition may be used in the form of a multilayer granulated product having an outer layer and an inner layer which are different in composition from each other, in order to control storage stability of the detergent composition or control the color of an appearance of the granules. For example, the inner portion of the respective pigment granules may be granulated as primary granules having a binder composition that allows the inner portion to collapse for a shorter period of time, whereas the outer layer of the respective pigment granules may be formed as a binder layer that allows the outer layer to collapse over a longer period of time. With such a multilayer configuration, the granules are free from collapse when applying merely a weak physical stimulus thereto, but undergo efficient collapse or dispersion when applying a strong physical stimulus thereto. Alternatively, when a pigment layer is formed in the inner layer or a titanium oxide layer or the other pigment layer is formed in the outer layer, it is possible to hide the color of subsequently produced colored foams until the detergent composition is foamed.

<Other Components>

The detergent composition of the present invention may also contain, in addition to the above pigment granules, optional components that may be used in ordinary detergent compositions, according to applications or objects of the detergent composition, unless the effects of the present invention are adversely affected. Examples of the optional components include a surfactant, an oil agent, a thickening agent, a humectant, a wetting agent, a colorant, an antiseptic agent, a sensitivity improver, a perfume, an antiphlogistic agent, a disinfectant, an ultraviolet absorber, an antioxidant, a converging agent, a whitening agent, drugs such as an anti-inflammatory agent, water, an alcohol, etc.

Examples of the anionic surfactant include fatty acid soaps, phosphoric acid ester-based surfactants, sulfuric acid ester-based surfactants, sulfonic acid-based surfactants, carboxylic acid-based surfactants, amino acid-based surfactants, sulfosuccinic acid-based surfactants, taurate-based surfactants, sugar-based surfactants, etc. Examples of the nonionic surfactant include ester-based surfactants, ether-based surfactants, ether ester-based surfactants, alkanol amide-based surfactants, alkylene glycol-based surfactants, etc. Examples of the amphoteric surfactant include imidazoline-based surfactants, betaine-based surfactants, acylamino acid-based surfactants, etc.

Examples of the oil agent include natural fatty acids such as lauric acid, myristic acid, palmitic acid, stearic acid, behenic acid, oleic acid, tall oil and lanolin fatty acids, synthetic fatty acids such as caproic acid, ester oils such as glycol distearate, etc.

Examples of the thickening agent include natural polymers such as xanthan gum, carageenan and alginic acid, semi-synthetic polymers such as sodium carboxymethyl cellulose, synthetic polymers such as carbomers as well as acrylic acid-based polymers such as polyacrylic acid, sodium polyacrylate and acrylic acid/alkyl methacrylate copolymers, etc.

Examples of the humectant include amino acids such as L-arginine, alanine and glycine, lipids having a moisture-retaining property such as betaine, pyrrolidone carboxylic acid, ceramides and phospholipids, plant extracts having a moisture-retaining effect such as aloe, *hypericum erectum* and okra, and natural products such as yogurt and honey, and extracts and fractions of these substances.

The dosage form or configuration of the detergent composition of the present invention is not particularly limited, and may be any of a solid, a liquid, a powder, a paste, a gel or the like.

The detergent composition of the present invention may be suitably used, for example, as facial cleansers, whole body cleansers such as body soaps, body shampoos and shower gels, hand soaps, hair shampoos, dish detergents, liquid laundry detergents, etc.

In addition, these detergent compositions may also be suitably used even when filled in a container having a color as a measure of foaming or in a transparent container.

[Process for Producing Detergent Composition]

The process for producing the detergent composition according to the present invention includes the steps of mixing and granulating a powder containing the pigment and a solution of the component (B) including at least one compound selected from the group consisting of polyvinyl alcohol, a polyvinyl alcohol derivative, polyvinyl pyrrolidone and a polyvinyl pyrrolidone derivative to obtain the aforementioned pigment granules, and mixing the thus obtained pigment granules with a detergent.

The method for producing the pigment granules is the same as described above.

The method of mixing the pigment granules with the detergent is not particularly limited. For example, the pigment granules are directly charged into the detergent, and then the resulting mixture is stirred using a homomixer, etc., whereby it is possible to readily produce the pigment granules as aimed.

With respect to the aforementioned embodiments of the present invention, there are described the following aspects concerning the detergent composition and the process for producing the detergent composition.

<1> A detergent composition including pigment granules containing (A) from 10 to 95% by mass of a water-insoluble pigment, and (B) at least two compounds selected from the group consisting of polyvinyl alcohol, a polyvinyl alcohol derivative, polyvinyl pyrrolidone and a polyvinyl pyrrolidone derivative.

<2> The detergent composition according to the aspect <1>, wherein a content of the water-insoluble pigment (A) in the pigment granules is preferably not less than 12% by mass, more preferably not less than 15% by mass, and even more preferably not less than 18% by mass, and is also preferably not more than 90% by mass, more preferably not more than 85% by mass, and even more preferably not more than 80% by mass.

<3> The detergent composition according to the aspect <1> or <2>, wherein a content of the water-insoluble pigment (A) in the pigment granules is from 12 to 90% by mass, preferably from 15 to 85% by mass, and more preferably from 18 to 80% by mass.

<4> The detergent composition according to any one of the aspects <1> to <3>, wherein the component (B) contains (b1) at least one compound selected from the group consisting of polyvinyl alcohol and a polyvinyl alcohol derivative which preferably have a viscosity of not less than 15 mPa·s, more preferably not less than 18 mPa·s, and even more preferably not less than 20 mPa·s as measured at 20° C. with respect to a 4% aqueous solution thereof using a B-type viscometer, and (b2) at least one compound selected from the group consisting of polyvinyl alcohol and polyvinyl pyrrolidone which preferably have a viscosity of less than 15 mPa·s, more preferably less than 13 mPa·s, and even more preferably less than 11 mPa·s as measured at 20° C. with respect to a 4% aqueous solution thereof.

<5> The detergent composition according to the aspect <4>, wherein the component (B) contains any of a combination of the polyvinyl alcohol derivative (b1) and the polyvinyl alcohol (b2), a combination of the polyvinyl alcohol derivative (b1) and the polyvinyl pyrrolidone (b2), and a combination of the polyvinyl alcohol (b1) and the polyvinyl pyrrolidone (b2).

<6> The detergent composition according to the aspect <4> or <5>, wherein a compounding mass ratio of the compound (b1) to the compound (b2) [(b1)/(b2)] is preferably not less than 0.05, more preferably not less than 0.1, and even more preferably not less than 0.15, and is also preferably not more than 3.0, more preferably not more than 2.5, and even more preferably not more than 2.0.

<7> The detergent composition according to any one of the aspects <1> to <6>, wherein the polyvinyl alcohol derivative as the component (B) contained in the pigment granules is at least one compound selected from the group consisting of an anion-modified polyvinyl alcohol derivative and a cation-modified polyvinyl alcohol derivative.

<8> The detergent composition according to the aspect <7>, wherein the anion-modified polyvinyl alcohol derivative is at least one compound selected from the group consisting of a carboxylic acid-modified polyvinyl alcohol, an undecylenic acid-modified polyvinyl alcohol and a sulfonic acid-modified polyvinyl alcohol.

<9> The detergent composition according to the aspect <7>, wherein the cation-modified polyvinyl alcohol derivative is at least one compound selected from the group consisting of an ammonium-modified polyvinyl alcohol, a sulfonium-modified polyvinyl alcohol and an amino group-modified polyvinyl alcohol.

<10> The detergent composition according to any one of the aspects <1> to <9>, wherein a content of the component (B) in the pigment granules is preferably not less than 0.05% by mass, more preferably not less than 0.1% by mass, and even more preferably not less than 0.5% by mass, and is also preferably not more than 50% by mass, more preferably not more than 30% by mass, and even more preferably not more than 15% by mass.

<11> The detergent composition according to any one of the aspects <1> to <10>, wherein a content of the component (B) is preferably not less than 0.05% by mass, more preferably not less than 0.1% by mass, even more preferably not less than 0.5% by mass, and is also preferably not more than 50% by mass, more preferably not more than 30% by mass, and even more preferably not more than 15% by mass.

<12> The detergent composition according to any one of the aspects <1> to <11>, further including an alcohol (C) selected from the group consisting of ethanol and polyhydric alcohols in an amount of not more than 5% by mass.

<13> The detergent composition according to any one of the aspects <1> to <12>, wherein an average particle size of the pigment granules is preferably not less than 20 μm, more preferably not less than 30 μm, and even more preferably not less than 50 μm, and is also preferably not more than 1500 μm, more preferably not more than 900 μm, and even more preferably not more than 800 μm.

<14> The detergent composition according to any one of the aspects <1> to <13>, wherein the pigment granules contain a water-insoluble powder.

<15> The detergent composition according to any one of the aspects <1> to <14>, wherein a content of the pigment granules in the detergent composition is preferably not less than 0.005% by mass, more preferably not less than 0.01% by mass, and even more preferably not less than 0.05% by mass, and is also preferably not more than 4% by mass, more preferably not more than 2% by mass, and even more preferably not more than 1% by mass.

<16> The detergent composition according to any one of the aspects <1> to <15>, wherein a concentration of the pigment in the detergent composition is preferably not less than 0.001% by mass, more preferably not less than 0.005% by mass, and even more preferably not less than 0.007% by mass, and is also preferably not more than 5% by mass, more preferably not more than 2% by mass, and even more preferably not more than 0.5% by mass.

<17> The detergent composition according to any one of the aspects <1> to <16>, wherein an electrical conductivity of a 5-fold diluted solution of the detergent composition is preferably not less than 0.1 S/m, more preferably not less than 0.2 S/m, even more preferably not less than 0.3 S/m, and further even more preferably not less than 0.5 S/m, and is also preferably not more than 1.7 S/m, more preferably not more than 1.5 S/m, even more preferably not more than 1.0 S/m, and further even more preferably not more than 0.8 S/m.

<18> A process for producing the detergent composition according to any one of the aspects <1> to <17>, including the steps of mixing and granulating a powder containing the water-insoluble pigment (A) and a solution of the component (B) to obtain a granulated product; drying the resulting granulated product to obtain the pigment granules; and mixing the pigment granules with a detergent.

EXAMPLES

In the following Examples and Comparative Examples, the terms "%" and "part(s)" represent "% by mass" and "part(s) by mass", respectively, unless otherwise noted.

Meanwhile, the average particle size of the pigment granules was measured by the following method.

<Measurement of Average Particle Size of Pigment Granules>

Using 12-stage sieves having mesh sizes of 2000 μm, 1400 μm, 1000 μm, 710 μm, 500 μm, 355 μm, 250 μm, 180 μm, 125 μm, 90 μm, 63 μm and 45 μm, respectively, as prescribed in JIS Z 8801-1 (established on May 20, 2000, finally revised on Nov. 20, 2006) and a receiving pan on which the sieves were stacked each other in the order of the mesh size from a smaller side, 100 g of the granules were added and placed on the uppermost 2000 μm sieve, followed by closing the sieves stacked on the receiving pan with a lid. The closed sieves and receiving pan were mounted to a low-tap sieve shaker (available from HEIKO Seisakusho Co., Ltd.; tapping: 156 times/min; rolling: 290 times/min), and vibrated for 5 min. Then, the masses of the granules remaining on the respective sieves and receiving pan were measured to calculate mass ratios (%) of the granules on the respective sieves and receiving pan. The mass ratios of the granules remaining on the receiving pan and the respective sieves were accumulated successively from the receiving pan to the respective sieves in the order of the mesh size from a smaller side until reaching 50% as a cumulative value thereof, and the particle size of the granules corresponding to the 50% cumulative value was defined as an average particle size of the granules.

Production Example 1 (Production of Pigment Granules (1))

A stirring granulator "FM-20 Model Henschel Mixer" (capacity: 20 L) available from Nippon Coke & Engineering, Co., Ltd., was charged with 0.8 kg of corn starch "Japanese Pharmacopoeia Corn Starch" (tradename) available from Matsutani Chemical Industry Co., Ltd., and 1.2 kg of a pigment "Red #226" (tradename) available from Kishi Kasei Co., Ltd., and the contents of the granulator were mixed for 5 min while operating a stirring blade at a rotating speed of 900 rpm (peripheral speed of a tip end of the stirring blade: 14 m/s). Then, 210 g of a 10% aqueous solution prepared by dissolving 10 parts by mass of a polyvinyl alcohol derivative "KM-118" (tradename) (maleic acid-modified PVA; average molecular weight: 80,000; viscosity of a 4% aqueous solution at 20° C.: 30 mPa·s) available from Kuraray Co., Ltd., in 90 parts by mass of purified water, and 630 g of a 10% aqueous solution prepared by dissolving 10 parts by mass of polyvinyl pyrrolidone "K-15" (tradename) (PVP; viscosity of a 4% aqueous solution at 20° C.: 5 mPa·s) available from International Specialty Products, Inc., in 90 parts by mass of purified water (temperature: 40° C.) were mixed with each other and added to the granulator, and the contents of the granulator were stirred for 6 min and then dried by hot air at 100° C. for 30 min. The resulting dried product was classified using a sieve, thereby obtaining pigment granules (1) (pigment content: 58%) having an average particle size shown in Tables 1, 2, 3 and 5.

Production Examples 2, 3, 10, 11 and 16 to 20 (Production of Pigment Granules (2), (3), (10), (11) and (16) to (20))

The same procedure as in Production Example 1 was repeated except that the combination and compositional ratios of the component (B) and the pigment compounded were changed as shown in Tables, thereby obtaining pigment granules (2), (3), (10), (11) and (16) to (20) respectively having an average particle size of 300 μm.

Production Example 4 (Production of Pigment Granules (4))

The same procedure as in Production Example 1 was repeated except that 630 g of a 10% aqueous solution prepared by dissolving 10 parts by mass of polyvinyl alcohol "GOHSENOL EG-05" (tradename) (average molecular weight: about 120,000; viscosity of a 4% aqueous solution at 20° C.: 44 mPa·s) available from Nippon Synthetic Chemical Industry Co., Ltd., in 90 parts by mass of purified water, and 210 g of a 10% aqueous solution prepared by dissolving 10 parts by mass of a polyvinyl alcohol derivative "KM-118" (tradename) (maleic acid-modified PVA; average molecular weight: 80,000; viscosity of a 4% aqueous solution at 20° C.: 30 mPa·s) available from Kuraray Co., Ltd., in 90 parts by mass of purified water (temperature: 40° C.) were added and used as the component (B), thereby obtaining pigment granules (4) having an average particle size of 300 μm.

Production Example 5 (Production of Pigment Granules (5))

The same procedure as in Production Example 1 was repeated except that 210 g of a 10% aqueous solution prepared by dissolving 10 parts by mass of polyvinyl alcohol "GOHSENOL EG-40" (tradename) (average molecular weight: about 30,000; viscosity of a 4% aqueous solution at 20° C.: 5 mPa·s) available from Nippon Synthetic Chemical Industry Co., Ltd., in 90 parts by mass of purified water, and 630 g of a 10% aqueous solution prepared by dissolving 10 parts by mass of polyvinyl pyrrolidone "K-15" (tradename) (PVP; viscosity of a 4% aqueous solution at 20° C.: 5 mPa·s) available from International Specialty Products, Inc., in 90 parts by mass of purified water (temperature: 40° C.) were added and used as the component (B), thereby obtaining pigment granules (5) having an average particle size of 300 μm.

Production Examples 6 to 9 (Production of Pigment Granules (6) to (9))

The same procedure as in Production Example 1 was repeated except that 840 g of a 10% aqueous solution prepared by dissolving 10 parts by mass of any of a polyvinyl alcohol derivative "KM-118" (tradename) (maleic acid-modified PVA; average molecular weight: 80,000; viscosity of a 4% aqueous solution at 20° C.: 30 mPa·s) available from Kuraray Co., Ltd., polyvinyl pyrrolidone "K-15" (tradename) (PVP; viscosity of a 4% aqueous solution at 20° C.: 5 mPa·s) available from International Specialty Products, Inc., polyvinyl alcohol "GOHSENOL EG-40" (tradename) (average molecular weight: about 120,000; viscosity of a 4% aqueous solution at 20° C.: 44 mPa·s) available from Nippon Synthetic Chemical Industry Co., Ltd., and polyvinyl alcohol "GOHSENOL EG-05" (tradename) (average molecular weight: about 30,000; viscosity of a 4% aqueous solution at 20° C.: 5 mPa·s) available from Nippon Synthetic Chemical Industry Co., Ltd., in 90 parts by mass of purified water (temperature: 40° C.) was added and used as the component (B), thereby obtaining pigment granules (6) to (9) respectively having an average particle size of 300 μm.

Production Examples 12 to 14 (Production of Pigment Granules (12) to (14))

A stirring granulator "FM-20 Model Henschel Mixer" (capacity: 20 L) available from Nippon Coke & Engineering, Co., Ltd., was charged with a predetermined amount (0.76 kg for pigment granules (12), 0.71 kg for pigment granules (13) or 0.63 kg for pigment granules (14)) of corn starch "Japanese Pharmacopoeia Corn Starch" (tradename) available from Matsutani Chemical Industry Co., Ltd., and 1.2 kg of a pigment "Red #226" (tradename) available from Kishi Kasei Co., Ltd., and the contents of the granulator were mixed for 5 min while operating a stirring blade at a rotating speed of 900 rpm (peripheral speed at a tip end of the stirring blade: 14 m/s). Then, 210 g of a 10% aqueous solution prepared by dissolving 10 parts by mass of a polyvinyl alcohol derivative "KM-118" (tradename) (maleic acid-modified PVA; average molecular weight: 80,000; viscosity of a 4% aqueous solution at 20° C.: 30 mPa·s) available from Kuraray Co., Ltd., in 90 parts by mass of purified water, and 630 g of a 10% aqueous solution prepared by dissolving 10 parts by mass of polyvinyl pyrrolidone "K-15" (tradename) (PVP; viscosity of a 4% aqueous solution at 20° C.: 5 mPa·s) available from International Specialty Products, Inc., in 90 parts by mass of purified water (temperature: 40° C.) were mixed with each other and added to the granulator, and further a predetermined amount (42 g for pigment granules (12), 84 g for pigment granules (13) or 168 g for pigment granules (14)) of concentrated glycerol was added to the granulator. The contents of the granulator were stirred for 6 min and then dried by hot air at 100° C. for 30 min. The resulting dried product was classified using a sieve, thereby obtaining pigment granules (12) to (14) respectively having an average particle size of 300 μm.

Production Example 15 (Production of Pigment Granules (15))

The same procedure as in Production Example 1 was repeated except that 210 g of a 10% aqueous solution prepared by dissolving 10 parts by mass of a polyvinyl alcohol derivative "CM-318" (tradename) (amino group-modified PVA; viscosity of a 4% aqueous solution at 20° C.: 22 mPa·s) available from Kuraray Co., Ltd., in 90 parts by mass of purified water, and 630 g of a 10% aqueous solution prepared by dissolving 10 parts by mass of polyvinyl pyrrolidone "K-15" (tradename) (PVP; viscosity of a 4% aqueous solution at 20° C.: 5 mPa·s) available from International Specialty Products, Inc., in 90 parts by mass of purified water (temperature: 40° C.) were added and used as the component (B), thereby obtaining pigment granules (15) having an average particle size of 300 μm.

Production Example 21 (Production of Pigment Granules (21))

The same procedure as in Production Example 1 was repeated except that β-carotene was used in place of the pigment "Red #226" (tradename) available from Kishi Kasei Co., Ltd., thereby obtaining pigment granules (21) having an average particle size of 300 μm.

Production Example 22 (Production of Pigment Granules (22))

The same procedure as in Production Example 1 was repeated except that black iron oxide was used in place of the pigment "Red #226" (tradename) available from Kishi Kasei Co., Ltd., thereby obtaining pigment granules (22) having an average particle size of 300 μm.

Production Example 23 (Production of Pigment Granules (23))

The same procedure as in Production Example 1 was repeated except for using 1 kg of a pigment "Red #226" (tradename), 0.2 kg of a 10% aqueous solution of polyvinyl alcohol "GOHSENOL EG-40" (tradename) (average molecular weight: about 120,000; viscosity of a 4% aqueous solution at 20° C.: 44 mPa·s) available from Nippon Synthetic Chemical Industry Co., Ltd., 0.3 kg of a 10% aqueous solution of a polyvinyl alcohol derivative "GOHSENEX T-330H" (tradename) (average molecular weight: about 100,000; viscosity of a 4% aqueous solution at 20° C.: 30 mPa·s) available from Nippon Synthetic Chemical Industry Co., Ltd., 0.5 kg of a 10% aqueous solution of polyvinyl pyrrolidone "K-15" (tradename), and 0.9 kg of corn starch, thereby obtaining pigment granules (23) (pigment content: 50%) having an average particle size of 400 μm.

Production Example 24 (Production of Pigment Granules (24))

A tabletop mixer "PANASONIC MX-X61-W" (tradename) available from Panasonic Corporation was charged with 65 g of a pigment "Red #226" (tradename) and 32 g of corn starch. The contents of the tabletop mixer were stirred for 5 min, and then 15 g of a 10% aqueous solution of a polyvinyl alcohol derivative "KM-118" (tradename) and 15 g of a 10% aqueous solution of polyvinyl alcohol "GOHSENOL EG-05" (tradename) (average molecular weight: about 30,000; viscosity of a 4% aqueous solution at 20° C.: 5 mPa·s) available from Nippon Synthetic Chemical Industry Co., Ltd., were mixed and added dropwise into the mixer while stirring, thereby obtaining a granulated product. The thus obtained granulated product was dried by hot air at 100° C. for 30 min. The resulting dried product was classified using a sieve, thereby obtaining pigment granules (24) (pigment content: 65%) having an average particle size of 300 μm.

Production Example 25 (Production of Pigment Granules (25))

The same procedure as in Production Example 24 was repeated except for using 78 g of a pigment "Red #226" (tradename), 20 g of corn starch, 10 g of a 10% aqueous solution of polyvinyl alcohol "GOHSENOL EG-40" (tradename) and 10 g of a 10% aqueous solution of polyvinyl pyrrolidone "K-15" (tradename), thereby obtaining pigment granules (25) (pigment content: 78%) having an average particle size of 600 μm.

Production Example 26 (Production of Pigment Granules (26))

The same procedure as in Production Example 24 was repeated except for using 30 g of a pigment "Red #226" (tradename), 66 g of corn starch, 15 g of a 10% aqueous solution of polyvinyl alcohol "KM-118" (tradename) and 25 g of a 10% aqueous solution of polyvinyl pyrrolidone "K-15" (tradename), thereby obtaining pigment granules (26) (pigment content: 30%) having an average particle size of 150 μm.

Examples 1 to 26 and Comparative Examples 1 to 12 (Body Soap)

Using the pigment granules obtained in the above Production Examples, body soaps having respective formulations shown in Tables 1 to 5 were prepared by an ordinary method and evaluated for the following items. The results are shown in Tables 1 to 5.
<Measurement of Electrical Conductivity of 5-Fold Diluted Solution>
The detergent composition was sampled in an amount of 10 g, and 40 g of purified water was added thereto, and the obtained solution was uniformly stirred to prepare a solution or viscous liquid as a sample. The sample was subjected to measurement of a conductivity at 25° C. using an electrical conductivity meter "EC METER CM-60G" available from DKK-TOA Corporation.
<Evaluation Using Colorimeter>
(1) Evaluation of Color of Detergent
One gram of the body soap obtained in the respective Examples and Comparative Examples was subjected to measurement of a color thereof using a colorimeter (D65 light source) available from Konica Minolta Optics Inc., and the color difference ΔE was calculated according to the above formula (1).
(2) Evaluation of Color of Foams
Nine grams of tap water (at 40° C.) was added to 1 g of the body soap obtained in the respective Examples and Comparative Examples, and the resulting solution was foamed for 30 sec using a foaming device "PANASONIC HAND MIXER MK-H4-W" available from Panasonic Corporation which was equipped with a net at a stirring section thereof. The resulting foams were filled in a 50 mL glass vessel to measure a color of the foams using a colorimeter (D65 light source) available from Konica Minolta Optics Inc., and the color difference ΔE was calculated according to the above formula (1).

<Sensory Evaluation by Panelists>
The body soap obtained in the respective Examples and Comparative Examples was used by panelists (5 persons) in an ordinary manner to conduct a sensory evaluation for "appearance of the body soap when put on their hands", "color of foams upon foaming", "foamability upon use" and "time required until color development of foams" according to the following evaluation ratings, and an average value of the points given by the five panelists in the above evaluation was determined.

Meanwhile, the "foamability upon use" was evaluated by comparison with the case where the body soap prepared from the detergent composition as a control (Comparative Example 1) was used.
(1) Evaluation for Appearance of Body Soap When Put on Hands
  4: Similar to an ordinary detergent;
  3: A detergent stock solution (bulk) was slightly colored, and usable without hesitation;
  2: A detergent stock solution (bulk) had a slightly deep color, and was usable merely with slight hesitation; and
  1: A detergent stock solution (bulk) had an excessively deep color, and a use thereof was disliked.
(2) Evaluation for Color of Foams Upon Foaming
  5: Foams were uniformly and very deeply colored;
  4: Foams were uniformly and deeply colored;
  3: Foams were thinly colored;
  2: Color development of foams was recognized only when watched intently; and
  1: Foams were just white.
(3) Evaluation for Foamability Upon Use
  4: Very good foamability;
  3: Good foamability;
  2: Poor foamability; and
  1: Very poor foamability.
(4) Time Required Until Color Development of Foams
The time at which the detergent was put on hands and foaming of the detergent was initiated was defined as a point of initiation of the measurement (starting point) at which a standard color (a*=3) was presented to the panelists. Then, the panelist were requested to notify the time at which the color of foams of the detergent became equal to the standard color, and the time was defined as a point of termination of the measurement (end point). The time interval between the starting point and the end point was measured to calculate an average value of the measured time intervals as the time required until color development of foams.
  5: Within 10 sec;
  4: From 11 to 30 sec;
  3: From 31 to 60 sec;
  2: From 61 to 90 sec;
  1; Not shorter than 91 sec; and
  X: Not colored until reaching the standard color (a*=3).
<Evaluation for Stability>
(1) Compounding Stability of Pigment Granules
The pigment granules used in the respective Examples and Comparative Examples were subjected to visual evaluation for stability upon compounding the granules into the detergent composition according to the following ratings.
  3: Compounded without any problem;
  2: Oozing-out of the pigment from the pigment granules occurred upon compounding, but the pigment granules were free from the change with time; and
  1: Oozing-out of the pigment from the pigment granules occurred upon compounding, and the change in particle size of the pigment granules and the change in color of the preparation occurred with time.

(2) Storage Stability

The body soaps obtained in the respective Examples and Comparative Examples were stored in a constant temperature oven at 45° C. for 2 weeks and then subjected to visual evaluation for storage stability of the preparation (such as separation and uniformity of granules and color) according to the following ratings.

3: Well stabilized;

2: Viscosity of the preparation tended to be lowered, but no change in appearance thereof was recognized; and 1: Undesirable changes such as separation of the preparation, precipitation and floating of the granules and color unevenness were recognized.

TABLE 1

| | Examples | | | | | Comparative Examples | | | |
|---|---|---|---|---|---|---|---|---|---|
| | 1 | 2 | 3 | 4 | 5 | 1 | 2 | 3 | 4 |
| Composition of detergent composition (%) | | | | | | | | | |
| Lauric acid | 6 | 6 | 6 | 6 | 6 | 6 | 6 | 6 | 6 |
| Myristic acid | 6 | 6 | 6 | 6 | 6 | 6 | 6 | 6 | 6 |
| Palmitic acid | 6 | 6 | 6 | 6 | 6 | 6 | 6 | 6 | 6 |
| Sodium POE (3) laurylethersulfate | 2.5 | 2.5 | 2.5 | 2.5 | 2.5 | 2.5 | 2.5 | 2.5 | 2.5 |
| Lauramide propyl betaine | 1.2 | 1.2 | 1.2 | 1.2 | 1.2 | 1.2 | 1.2 | 1.2 | 1.2 |
| Glycol distearate | 2 | 2 | 2 | 2 | 2 | 2 | 2 | 2 | 2 |
| Concentrated glycerol | 10 | 10 | 10 | 10 | 10 | 10 | 10 | 10 | 10 |
| Carbomer | 2 | 2 | 2 | 2 | 2 | 2 | 2 | 2 | 2 |
| Purified water | bal. | bal. | bal. | bal. | bal. | bal. | bal. | bal. | bal. |
| Potassium hydroxide aqueous solution*[1] | 5 | 5 | 5 | 5 | 5 | 5 | 5 | 5 | 5 |
| Red #227 (Fast Acid Magenta) | — | — | — | — | — | — | — | — | — |
| Red #226 (Helindone Pink CN) | — | — | — | — | — | — | — | — | — |
| Pigment granules/average particle size: 300 μm | 0.173 | 0.264 | 0.53 | 0.173 | 0.173 | — | 0.173 | 0.173 | 0.173 |
| Composition of pigment granules (%) | | | | | | | | | |
| No. of pigment granules produced in Production Examples | (1) | (2) | (3) | (4) | (5) | — | (6) | (7) | (8) |
| Red #227 | — | — | — | — | — | — | — | — | — |
| Red #226 | 58 | 38 | 19 | 58 | 58 | — | 58 | 58 | 58 |
| PVA ("GOHSENOL EG-05" (tradename)) | — | — | — | 3 | — | — | — | 4 | — |
| PVA ("GOHSENOL EG-40" (tradename)) | — | — | — | — | 1 | — | 4 | — | — |
| PVA derivative ("KM-118" (tradename)) | 1 | 1 | 1 | 1 | — | — | — | — | 4 |
| PVP ("K-15" (tradename)) | 3 | 3 | 3 | — | 3 | — | — | — | — |
| Corn starch | 38 | 58 | 77 | 38 | 38 | — | 38 | 38 | 38 |
| Content of pigment in detergent composition (%) | 0.1 | 0.1 | 0.1 | 0.1 | 0.1 | — | 0.1 | 0.1 | 0.1 |
| Electrical conductivity of 5-fold diluted solution (S/m) | 0.773 | 0.773 | 0.773 | 0.773 | 0.773 | 0.773 | 0.773 | 0.773 | 0.773 |
| Evaluation results <Evaluation by colorimeter: ΔE> | | | | | | | | | |
| Detergent stock solution | 4.7 | 5.1 | 7.5 | 4.2 | 5.2 | 0.0 | 5.8 | 9.0 | 3.0 |
| Color of foams | 3.3 | 4.5 | 4.2 | 5.1 | 5.4 | 0.0 | 3.4 | 6.9 | 1.2 |
| <Sensory evaluation by panelists> | | | | | | | | | |
| Impression of appearance when put on hands | 4 | 4 | 3.6 | 4 | 4 | 4 | 4 | 2.8 | 4 |
| Color of foams upon foaming | 4 | 4 | 3.6 | 4 | 4 | 1 | 3.4 | 3.6 | 2.4 |
| Foamability | 3.6 | 3.4 | 2.8 | 3.6 | 3.4 | 3.4 | 3.6 | 3.4 | 3.8 |
| Time required until color development of foams | 4 | 4 | 3.6 | 4 | 4 | X | 1 | 5 | 1 |

TABLE 1-continued

| <Evaluation for stability> | | | | | | | | | |
|---|---|---|---|---|---|---|---|---|---|
| Compounding stability of granules | 3 | 3 | 3 | 3 | 3 | — | 3 | 1 | 3 |
| Storage stability | 3 | 3 | 3 | 3 | 3 | 3 | 3 | 2 | 3 |

| | Comparative Examples | | | | | | | |
|---|---|---|---|---|---|---|---|---|
| | 5 | 6 | 7 | 8 | 9 | 10 | 11 | 12 |
| Composition of detergent composition (%) | | | | | | | | |
| Laurie acid | 6 | 6 | 6 | 6 | 6 | 6 | 6 | 6 |
| Myristic acid | 6 | 6 | 6 | 6 | 6 | 6 | 6 | 6 |
| Palmitic acid | 6 | 6 | 6 | 6 | 6 | 6 | 6 | 6 |
| Sodium POE (3) laurylethersulfate | 2.5 | 2.5 | 2.5 | 2.5 | 2.5 | 2.5 | 2.5 | 2.5 |
| Lauramide propyl betaine | 1.2 | 1.2 | 1.2 | 1.2 | 1.2 | 1.2 | 1.2 | 1.2 |
| Glycol distearate | 2 | 2 | 2 | 2 | 2 | 2 | 2 | 2 |
| Concentrated glycerol | 10 | 10 | 10 | 10 | 10 | 10 | 10 | 10 |
| Carbomer | 2 | 2 | 2 | 2 | 2 | 2 | 2 | 2 |
| Purified water | bal. | bal. | bal. | bal. | bal. | bal. | bal. | bal. |
| Potassium hydroxide aqueous solution*1 | 5 | 5 | 5 | 5 | 5 | 5 | 5 | 5 |
| Red #227 (Fast Acid Magenta) | — | — | — | 0.1 | 0.01 | — | — | — |
| Red #226 (Helindone Pink CN) | — | — | — | — | — | 0.1 | 0.01 | — |
| Pigment granules/average particle size: 300 μm | 0.173 | 2 | 0.2 | — | — | — | — | 0.264 |
| Composition of pigment granules (%) | | | | | | | | |
| No. of pigment granules produced in Production Examples | (9) | (10) | (10) | — | — | — | — | (11) |
| Red #227 | — | — | — | — | — | — | — | 38 |
| Red #226 | 58 | 5 | 5 | — | — | — | — | — |
| PVA ("GOHSENOL EG-05" (tradename)) | — | — | — | — | — | — | — | — |
| PVA ("GOHSENOL EG-40" (tradename)) | — | — | — | — | — | — | — | — |
| PVA derivative ("KM-118" (tradename)) | — | 1 | 1 | — | — | — | — | 3 |
| PVP ("K-15" (tradename)) | 4 | 3 | 3 | — | — | — | — | 1 |
| Corn starch | 38 | 91 | 91 | — | — | — | — | 58 |
| Content of pigment in detergent composition (%) | 0.1 | 0.1 | 0.01 | 0.1 | 0.01 | 0.1 | 0.01 | 0.1 |
| Electrical conductivity of 5-fold diluted solution (S/m) | 0.773 | 0.773 | 0.773 | 0.773 | 0.773 | 0.773 | 0.773 | 0.773 |
| Evaluation results <Evaluation by colorimeter: ΔE> | | | | | | | | |
| Detergent stock solution | 12.0 | 29.2 | 10.5 | 61.9 | 40.6 | 54.8 | 45.8 | 59.6 |
| Color of foams | 10.2 | 5.8 | 0.4 | 26.8 | 6.5 | 6.8 | 2.5 | 30.0 |
| <Sensory evaluation by panelists> | | | | | | | | |
| Impression of appearance when put on hands | 2 | 2.4 | 3.6 | 1 | 1.2 | 1.8 | 1.8 | 1 |
| Color of foams upon foaming | 4.6 | 4 | 1 | 5 | 3.8 | 5 | 2 | 5 |
| Foam ability | 2.2 | 2 | 3 | 2.6 | 3.2 | 1.8 | 2.4 | 3 |
| Time required until color development of foams | 5 | 4 | X | 5 | 5 | 5 | X | 5 |

TABLE 1-continued

| <Evaluation for stability> | | | | | | | | |
|---|---|---|---|---|---|---|---|---|
| Compounding stability of granules | 1 | 3 | 3 | — | — | — | — | 1 |
| Storage stability | 1 | 3 | 3 | 2 | 1 | 2 | 2 | 1 |

Note
[*1]Controlled such that the degree of neutralization was 98%.

As apparently recognized from Table 1, the body soaps obtained in Examples 1 to 5 could be prevented from suffering from coloration of the preparation itself, and were excellent in all of properties including coloration of foams upon use, foamability, time required until color development of foams and stability. On the other hand, the body soaps obtained in Comparative Examples 8 to 11 in which the non-granulated pigments were compounded, and the body soap obtained in Comparative Example 12 in which the pigment granules prepared using the water-soluble pigment were compounded, all suffered from excessively deep coloration of the preparation itself, and were deteriorated in storage stability. In addition, the body soaps obtained in Comparative Examples 6 and 7 in which the content of the pigment in the pigment granules was as low as 5% by mass, were insufficient in coloration of foams.

TABLE 2

| | Examples | | | | |
|---|---|---|---|---|---|
| | 1 | 6 | 7 | 8 | 9 |
| Composition of detergent composition (%) | | | | | |
| Lauric acid | 6 | 6 | 6 | 6 | 6 |
| Myristic acid | 6 | 6 | 6 | 6 | 6 |
| Palmitic acid | 6 | 6 | 6 | 6 | 6 |
| Sodium POE (3) laurylethersulfate | 2.5 | 2.5 | 2.5 | 2.5 | 2.5 |
| Lauramide propyl betaine | 1.2 | 1.2 | 1.2 | 1.2 | 1.2 |
| Glycol distearate | 2 | 2 | 2 | 2 | 2 |
| Concentrated glycerol | 10 | 10 | 10 | 10 | 10 |
| Carbomer | 2 | 2 | 2 | 2 | 2 |
| Purified water | bal. | bal. | bal. | bal. | bal. |
| Potassium hydroxide aqueous solution[*1] | 5 | 5 | 5 | 5 | 5 |
| Pigment granules/average particle size: 300 μm | 0.173 | 0.173 | 0.173 | 0.173 | 0.173 |
| Composition of pigment granules (%) | | | | | |
| No. of pigment granules produced in Production Examples | (1) | (12) | (13) | (14) | (15) |
| Red #226 (%) | 58 | 58 | 58 | 58 | 58 |
| PVA derivative ("KM-118" (tradename)) | 1 | 1 | 1 | 1 | — |
| PVA derivative ("CM-318" (tradename)) | — | — | — | — | 1 |
| PVP ("K-15" (tradename)) | 3 | 3 | 3 | 3 | 3 |
| Corn starch (%) | 38 | 36 | 34 | 30 | 38 |
| Concentrated glycerol (%) | — | 2 | 4 | 8 | — |
| Content of pigment in detergent composition (%) | 0.1 | 0.1 | 0.1 | 0.1 | 0.1 |
| Electrical conductivity of 5-fold diluted solution (S/m) | 0.773 | 0.773 | 0.773 | 0.773 | 0.773 |
| Evaluation results <Evaluation by colorimeter: ΔE> | | | | | |
| Detergent stock solution | 4.7 | 4.9 | 5.8 | 7.5 | 4.4 |
| Color of foams | 3.3 | 5.7 | 6.0 | 6.4 | 3.2 |

TABLE 2-continued

|  | Examples | | | | |
| --- | --- | --- | --- | --- | --- |
|  | 1 | 6 | 7 | 8 | 9 |
| <Sensory evaluation by panelists> | | | | | |
| Impression of appearance when put on hands | 4 | 4 | 3.6 | 3.2 | 3.2 |
| Color of foams upon foaming | 4 | 4 | 4 | 4 | 3.2 |
| Foamability | 3.6 | 3.6 | 3.4 | 3 | 2.4 |
| Time required until color development of foams | 4 | 4 | 4 | 5 | 3 |
| <Evaluation for stability> | | | | | |
| Compounding stability of granules | 3 | 3 | 2 | 1 | 3 |
| Storage stability | 3 | 3 | 3 | 1 | 2 |

Note
[*1] Controlled such that the degree of neutralization was 98%.

As apparently recognized from Table 2, the body soaps obtained in Examples 1 and 6 to 9 could be prevented from suffering from coloration of the preparation itself, and exhibited excellent properties as to coloration of foams upon use, foamability and stability, but it was estimated that the stability of the pigment granules was adversely influenced as the amount of the concentrated glycerol contained in the pigment granules was increased.

TABLE 3

|  | Examples | | | |
| --- | --- | --- | --- | --- |
|  | 1 | 10 | 11 | 12 |
| Composition of detergent composition (%) | | | | |
| Lauric acid | 6 | 6 | 2 | 2 |
| Myristic acid | 6 | 16 | 2 | 2 |
| Palmitic acid | 6 | 2 | 2 | 2 |
| Stearic acid | — | 3 | — | — |
| Sodium POE (3) laurylethersulfate | 2.5 | 2.5 | 0.8 | 0.8 |
| Lauramide propyl betaine | 1.2 | 1.2 | 0.4 | 0.4 |
| Glycol distearate | 2 | 2 | 2 | 2 |
| Concentrated glycerol | 10 | 35 | 4 | 4 |
| Carbomer | 2 | — | 2 | 2 |
| Sodium chloride | — | — | 1 | 5 |
| Purified water | bal. | bal. | bal. | bal. |
| Potassium hydroxide aqueous solution[*1] | 5 | 5 | 5 | 5 |
| Pigment granules/average particle size: 300 μm | 0.173 | 0.173 | 0.173 | 0.173 |
| Composition of pigment granules | | | | |
| No. of pigment granules produced in Production Examples | (1) | (1) | (1) | (1) |
| Red #226 (%) | 58 | 58 | 58 | 58 |
| PVA derivative ("KM-118" (tradename)) | 1 | 1 | 1 | 1 |
| PVP ("K-15" (tradename)) | 3 | 3 | 3 | 3 |
| Corn starch (%) | 38 | 38 | 38 | 38 |
| Content of pigment in detergent composition (%) | 0.1 | 0.1 | 0.1 | 0.1 |
| Electrical conductivity of 5-fold diluted solution (S/m) | 0.773 | 0.586 | 0.682 | 1.802 |
| Evaluation results <Evaluation by colorimeter: ΔE> | | | | |
| Detergent stock solution | 4.7 | 6.4 | 3.8 | 6.1 |
| Color of foams | 3.3 | 5.5 | 5.6 | 1.5 |
| <Sensory evaluation by panelists> | | | | |
| Impression of appearance when put on hands | 4 | 4 | 4 | 4 |
| Color of foams upon foaming | 4 | 4 | 4 | 2.4 |
| Foamability | 3.6 | 4 | 3 | 3 |
| Time required until color development of foams | 4 | 4 | 4 | 1.6 |
| <Evaluation for stability> | | | | |
| Compounding stability of granules | 3 | 3 | 3 | 3 |
| Storage stability | 3 | 3 | 3 | 3 |

Note
[*1] Controlled such that the degree of neutralization was 98%.

As apparently recognized from Table 3, it was estimated that as the electrical conductivity of the 5-fold diluted solution was excessively increased, the collapsibility of the pigment granules was adversely influenced upon use.

TABLE 4

|  | Examples | | | | | Comparative Examples | |
|---|---|---|---|---|---|---|---|
|  | 13 | 14 | 15 | 16 | 17 | 4 | 5 |
| Composition of detergent composition (%) | | | | | | | |
| Lauric acid | 6 | 6 | 6 | 6 | 6 | 6 | 6 |
| Myristic acid | 6 | 6 | 6 | 6 | 6 | 6 | 6 |
| Palmitic acid | 6 | 6 | 6 | 6 | 6 | 6 | 6 |
| Stearic acid | — | — | — | — | — | — | — |
| Sodium POE (3) laurylethersulfate | 2.5 | 2.5 | 2.5 | 2.5 | 2.5 | 2.5 | 2.5 |
| Lauramide propyl betaine | 1.2 | 1.2 | 1.2 | 1.2 | 1.2 | 1.2 | 1.2 |
| Glycol distearate | 2 | 2 | 2 | 2 | 2 | 2 | 2 |
| Concentrated glycerol | 10 | 10 | 10 | 10 | 10 | 10 | 10 |
| Carbomer | 2 | 2 | 2 | 2 | 2 | 2 | 2 |
| Sodium chloride | — | — | — | — | — | — | — |
| Purified water | bal. | bal. | bal. | bal. | bal. | bal. | bal. |
| Potassium hydroxide aqueous solution*[1] | 5 | 5 | 5 | 5 | 5 | 5 | 5 |
| Pigment granules/average particle size: 300 μm | 0.173 | 0.173 | 0.173 | 0.173 | 0.173 | 0.173 | 0.173 |
| Composition of pigment granules (%) | | | | | | | |
| No. of pigment granules produced in Production Examples | (16) | (17) | (18) | (19) | (20) | (8) | (9) |
| Red #226 (%) | 58 | 58 | 58 | 58 | 58 | 58 | 58 |
| (b1) PVA derivative ("KM-118" (tradename)) | 2.8 | 2 | 1.2 | 0.8 | 0.4 | 4 | 0 |
| (b2) PVP ("K-15" (tradename)) | 1.2 | 2 | 2.8 | 3.2 | 3.6 | 0 | 4 |
| Corn starch (%) | 38 | 38 | 38 | 38 | 38 | 38 | 38 |
| (b1)/(b2) | 2.333 | 1 | 0.429 | 0.25 | 0.111 | — | — |
| Content of pigment in detergent composition (%) | 0.1 | 0.1 | 0.1 | 0.1 | 0.1 | 0.1 | 0.1 |
| Electrical conductivity of 5-fold diluted solution (S/m) | 0.773 | 0.773 | 0.773 | 0.773 | 0.773 | 0.773 | 0.773 |
| Evaluation results <Evaluation by colorimeter: ΔE> | | | | | | | |
| Detergent stock solution | 3.0 | 3.1 | 3.2 | 4.3 | 5.3 | 3.0 | 12.0 |
| Color of foams | 2.4 | 3.3 | 3.9 | 5.4 | 7.2 | 1.2 | 10.2 |
| <Sensory evaluation by panelists> | | | | | | | |
| Impression of appearance when put on hands | 4 | 4 | 4 | 4 | 4 | 4 | 2 |
| Color of foams upon foaming | 3.6 | 4 | 4 | 4 | 4.2 | 2.4 | 4.6 |
| Foamability | 3.8 | 3.6 | 3.6 | 3.6 | 3.4 | 3.8 | 2.2 |
| Time required until color development of foams | 2.8 | 3.8 | 4 | 4 | 4.4 | 1 | 5 |
| <Evaluation for stability> | | | | | | | |
| Compounding stability of granules | 3 | 3 | 3 | 3 | 2 | 3 | 1 |
| Storage stability | 3 | 3 | 3 | 3 | 3 | 3 | 1 |

Note
*[1]Controlled such that the degree of neutralization was 98%;
(b1): PVA derivative ("KM-118" (tradename); viscosity of 4% aqueous solution: 32 mPa · s/25° C.)
(b1): PVP ("K-15" (tradename); viscosity of 4% aqueous solution: 5 mPa · s/25° C.)

As apparently recognized from Table 4, with respect to the component (B) used in the pigment granules, the compounding mass ratio [(b1)/(b2)] had a large influence on efficient control of stability of the granules in the detergent and collapsibility of the granules upon use.

TABLE 5

|  | Examples | | | | | | | | | |
|---|---|---|---|---|---|---|---|---|---|---|
|  | 1 | 18 | 19 | 20 | 21 | 22 | 23 | 24 | 25 | 26 |
| Composition of detergent composition (%) | | | | | | | | | | |
| Lauric acid | 6 | 6 | 6 | 6 | 6 | 6 | 6 | 6 | 6 | 6 |
| Myristic acid | 6 | 6 | 6 | 6 | 6 | 6 | 6 | 6 | 6 | 6 |
| Palmitic acid | 6 | 6 | 6 | 6 | 6 | 6 | 6 | 6 | 6 | 6 |

TABLE 5-continued

| | Examples | | | | | | | | | |
|---|---|---|---|---|---|---|---|---|---|---|
| | 1 | 18 | 19 | 20 | 21 | 22 | 23 | 24 | 25 | 26 |
| Sodium POE (3) laurylethersulfate | 2.5 | 2.5 | 2.5 | 2.5 | 2.5 | 2.5 | 2.5 | 2.5 | 2.5 | 2.5 |
| Lauramide propyl betaine | 1.2 | 1.2 | 1.2 | 1.2 | 1.2 | 1.2 | 1.2 | 1.2 | 1.2 | 1.2 |
| Glycol distearate | 2 | 2 | 2 | 2 | 2 | 2 | 2 | 2 | 2 | 2 |
| Concentrated glycerol | 10 | 10 | 10 | 10 | 10 | 10 | 10 | 10 | 10 | 10 |
| Carbomer | 2 | 2 | 2 | 2 | 2 | 2 | 2 | 2 | 2 | 2 |
| Purified water | bal. | bal. | bal. | bal. | bal. | bal. | bal. | bal. | bal. | bal. |
| Potassium hydroxide aqueous solution*[1] | 5 | 5 | 5 | 5 | 5 | 5 | 5 | 5 | 5 | 5 |
| Pigment granules/average particle size: 30 μm | — | 0.173 | — | — | — | — | — | — | — | — |
| Pigment granules/average particle size: 75 μm | — | — | 0.173 | — | — | — | — | — | — | — |
| Pigment granules/average particle size: 300 μm | 0.173 | — | — | — | 0.345 | 0.173 | 0.017 | 0.345 | 0.086 | 3.45 |
| Pigment granules/average particle size: 800 μm | — | — | — | 0.173 | — | — | — | — | — | — |
| Composition of pigment granules (%) | | | | | | | | | | |
| No. of pigment granules produced in Production Examples | (1) | (1) | (1) | (1) | (21) | (22) | (1) | (1) | (1) | (1) |
| β-Carotene | — | — | — | — | 58 | — | — | — | — | — |
| Red #226 (%) | 58 | 58 | 58 | 58 | — | — | 58 | 58 | 58 | 58 |
| Black iron oxide | — | — | — | — | — | 58 | — | — | — | — |
| PVA derivative ("KM-118" (tradename)) | 1 | 1 | 1 | 1 | 1 | 1 | 1 | 1 | 1 | 1 |
| PVP ("K-15" (tradename)) | 3 | 3 | 3 | 3 | 3 | 3 | 3 | 3 | 3 | 3 |
| Corn starch | 38 | 38 | 38 | 38 | 38 | 38 | 38 | 38 | 38 | 38 |
| Content of pigment in detergent composition (%) | 0.1 | 0.1 | 0.1 | 0.1 | 0.2 | 0.1 | 0.01 | 0.2 | 0.05 | 2.0 |
| Electrical conductivity of 5-fold diluted solution (S/m) | 0.773 | 0.773 | 0.773 | 0.773 | 0.773 | 0.773 | 0.773 | 0.773 | 0.773 | 0.773 |
| Evaluation results | | | | | | | | | | |
| <Evaluation by colorimeter: ΔE> | | | | | | | | | | |
| Detergent stock solution | 4.7 | 20.3 | 12.5 | 3.4 | 5.5 | 3.2 | 4.1 | 7.8 | 3.0 | 28.7 |
| Color of foams | 3.3 | 8.4 | 5.0 | 3.0 | 7.4 | 3.7 | 2.2 | 12.0 | 1.9 | 27.5 |
| <Sensory evaluation by panelists> | | | | | | | | | | |
| Impression of appearance when put on hands | 4 | 2.8 | 3 | 4 | 4 | 4 | 4 | 3.4 | 4 | 2 |
| Color of foams upon foaming | 4 | 4.2 | 4 | 3.4 | 3.6 | 4 | 2.8 | 4.4 | 2.8 | 5 |
| Foamability | 3.6 | 2.4 | 3 | 2.6 | 3.6 | 3.4 | 3.4 | 3.6 | 3.2 | 2.6 |
| Time required until color development of foams | 4 | 4.4 | 4.2 | 4 | 3.8 | 4.6 | 4 | 4.6 | 3 | 5 |
| <Evaluation for stability> | | | | | | | | | | |
| Compounding stability of granules | 3 | 2 | 2 | 2 | 3 | 3 | 3 | 2 | 3 | 2 |
| Storage stability | 3 | 2 | 2 | 3 | 3 | 3 | 3 | 3 | 3 | 3 |

Note
*[1]Controlled such that the degree of neutralization was 98%;

As apparently recognized from Table 5, the body soaps obtained in Examples 18 to 26 all could be prevented from suffering from coloration of the preparation itself, and exhibited excellent properties as to coloration of foams upon use, foamability and stability.

Example 27 (Hair Shampoo)

The hair shampoo having the following composition was prepared by an ordinary method (pH 6/25° C.), and subjected to the same evaluation as described above. As a result, it was confirmed that the thus prepared hair shampoo could be prevented from suffering from coloration of the preparation itself, and exhibited excellent properties as to all of coloration of foams upon use, impression of an appearance of the preparation when put on hands, foamability and stability. Further, the electrical conductivity of the 5-fold diluted solution obtained in Example 27 was 0.533 S/m.

| (Components) | Compounding amount (% by mass) |
|---|---|
| Sodium POE (2) laurylethersulfate | 5.0 |
| Sodium POE (3) lauryletheracetate | 5.0 |
| Hydroxyalkyl hydroxyethyl sarcosine | 5.0 |
| 1,3-Butylene glycol | 2.0 |
| Lauric acid monoisopropanol amide | 1.0 |
| Ethylene glycol distearate | 2.0 |
| POE cetyl ether ("N-BC-15TX" (tradename) available from Nippon Surfactant Kogyo K.K.) | 1.0 |
| Cationized cellulose ("LEOGARD GP" (tradename) available from Lion Corporation) | 0.2 |
| Cationized fenugreek gum ("CATINAL CF-100" (tradename) available from Toho Chemical Industry Co., Ltd.) | 0.2 |
| Disodium edetate | 0.2 |
| Phenoxy ethanol | 0.2 |
| Sodium benzoate | 0.4 |

| (Components) | Compounding amount (% by mass) |
|---|---|
| (Ammonium acryloyl dimethyl taurine/ammonium carboxyethyl acrylate) crosspolymer ("Aristoflex TAC" (tradename) available from Clariant Corporation) | 0.2 |
| Solution of dimethyl diallyl ammonium chloride/acrylamide copolymer ("MERQUAT 550" (tradename) available from Calgon Carbon Corporation) | 0.5 |
| Dipotassium glycyrrhizate | 0.1 |
| Isopropyl methyl phenol | 0.1 |
| Citric acid | q.s. |
| Carrot extract ("CARROT EXTRACT BG" (tradename) available from Maruzen Pharmaceuticals Co., Ltd.) | 0.1 |
| Bark extract ("BARAK LIQUID B" (tradename) available from ICHIMARU PHARCOS Co., Ltd.) | 0.1 |
| Olive oil | 0.1 |
| Dimechiconol | 1.0 |
| Menthol | 0.1 |
| Pigment granules (produced in Production Example 23 in which the content of the pigment component in the pigment granules was adjusted to 50%) | 0.2 |
| Perfume | q.s. |
| Purified water | balance |

Example 28 (Hair Shampoo)

The hair shampoo having the following composition was prepared by an ordinary method (pH 6/25° C.), and subjected to the same evaluation as described above. As a result, it was confirmed that the thus prepared hair shampoo could be prevented from suffering from coloration of the preparation itself, and exhibited excellent properties as to all of coloration of foams upon use, impression of an appearance of the preparation when put on hands, foamability and stability. Further, the electrical conductivity of the 5-fold diluted solution obtained in Example 28 was 0.702 S/m.

| (Components) | Compounding amount (% by mass) |
|---|---|
| Sodium POE (2) laurylethersulfate | 10.0 |
| Solution of lauric acid amide propyl betaine | 3.0 |
| Solution of sodium lauroyl methyl-β-alanine | 3.0 |
| Dipropylene glycol | 4.0 |
| Lauric acid monoisopropanol amide | 1.0 |
| Ethylene glycol distearate | 1.5 |
| Cellulose derivative ("CATINAL HC-200" (tradename) available from Toho Chemical Industry Co., Ltd.) | 0.3 |
| Disodium edetate | 0.2 |
| Paraben | 0.1 |
| Phenoxy ethanol | 0.1 |
| Sodium benzoate | 0.4 |
| Carbomer ("Carbopol Aqua SF-2" (tradename) available from Akzo Nobel N.V.) | 2.0 |
| Solution of dimethyl diallyl ammonium chloride/acrylamide copolymer ("MERQUAT 550" (tradename) available from ONDEO Nalco Co., Ltd.) | 2.0 |
| Dipotassium glycyrrhizate | 0.1 |
| Isopropyl methyl phenol | 0.1 |
| Citric acid | q.s. |
| Honey | 0.1 |
| Hydrolyzed silk solution ("Promois Silk-1000" (tradename) available from Seiwa Kasei Co., Ltd.) | 0.1 |
| Swertia pseudochinensis extract ("Swertia Pseudochinensis Extract" (tradename) available from Maruzen Pharmaceuticals Co., Ltd.) | 0.1 |
| Aqueous emulsion of dimethicone ("BY22-083" (tradename) available from Dow Corning Toray Co., Ltd.) | 0.5 |
| Pigment granules (produced in Production Example 24 in which the content of the pigment component in the pigment granules was adjusted to 65%) | 0.1 |
| Yellow #4 | 0.0002 |
| Perfume | q.s. |
| Purified water | balance |

Example 29 (Body Shampoo)

The body shampoo having the following composition was prepared by an ordinary method (pH 6/25° C.), and subjected to the same evaluation as described above. As a result, it was confirmed that the thus prepared body shampoo was prevented from suffering from coloration of the preparation itself, and exhibited excellent properties as to all of coloration of foams upon use, impression of an appearance of the preparation when put on hands, foamability and stability. Further, the electrical conductivity of the 5-fold diluted solution obtained in Example 29 was 0.688 S/m.

| (Components) | Compounding amount (% by mass) |
|---|---|
| Sodium POE (3) laurylethersulfate | 10.0 |
| Triethanol amine lauryl sulfate | 5.0 |
| Lauric acid amide propyl betaine | 3.0 |
| Triethanol amine N-coconut oil fatty acid acyl-DL-alanine | 0.5 |
| POE cetyl ether ("N-BC-10TX" (tradename) available from Nippon Surfactant Kogyo K.K.) | 1.0 |
| Lauric acid monoisopropanol amide | 1.0 |
| POE cetostearyl hydroxymyristylene ether ("ELFACOS GT282S" (tradename) available from AKZO NOBEL N.V.) | 0.1 |
| Carbomer | 1.5 |
| Solution of dimethyl diallyl ammonium chloride/acrylamide copolymer ("MERQUAT 550" (tradename) available from Nalco Co., Ltd.) | 1.0 |
| Disodium edetate | 0.2 |
| Salicylic acid | 0.1 |
| Paraben | 0.1 |
| Phenoxy ethanol | 0.2 |
| Olive oil | 0.2 |
| Almond oil | 0.1 |
| Dimethiconol (100 mm$^2$/s; 25° C.) | 1.2 |
| Kiwifruit extract ("Kiwifruit Extract" (tradename) available from Koei Kogyo Co., Ltd.) | 0.1 |
| Citric acid | q.s. |
| Pigment granules (produced in Production Example 1 in which the content of the pigment component in the pigment granules was adjusted to 58%) | 0.1 |
| Perfume | q.s. |
| Purified water | balance |

Example 30 (Body Soap)

The body soap having the following composition was prepared by an ordinary method (pH 9/25° C.), and subjected to the same evaluation as described above. As a result, it was confirmed that the thus prepared body soap was prevented from suffering from coloration of the preparation itself, and exhibited excellent properties as to all of coloration of foams upon use, impression of an appearance of the preparation when put on hands, foamability and stability. Further, the electrical conductivity of the 5-fold diluted solution obtained in Example 30 was 0.797 S/m.

| (Components) | Compounding amount (% by mass) |
|---|---|
| Lauric acid | 8.0 |
| Myristic acid | 5.0 |
| Palmitic acid | 5.0 |
| Sodium POE (3) laurylethersulfate | 5.0 |
| Palm kernel oil fatty acid amide propyl betaine | 1.0 |
| Guar gum derivative ("CATINAL CG-100" (tradename) available from Toho Chemical Industry Co., Ltd.) | 0.1 |
| Solution of acrylamide/acrylic acid/dimethyl diallyl ammonium chloride copolymer ("MERQUAT PLUS 3330" (tradename) available from Nalco Co., Ltd.) | 1.0 |
| Solution of dimethyl diallyl ammonium chloride/acrylamide copolymer ("MERQUAT 550" (tradename) available from Nalco Co., Ltd.) | 1.0 |
| Carbomer ("Carbopol Aqua SF-1" (tradename)) | 2.5 |
| Ethylene glycol distearate | 2.0 |
| Hydroxypropyl methyl cellulose | 0.5 |
| Hydrolyzed conchiolin ("PEARL PROTEIN EXTRACT BG-J" (tradename) available from Maruzen Pharmaceuticals Co., Ltd.) | 0.1 |
| Peach leaf extract ("PEACH EXTRACT" (tradename) available from Maruzen Pharmaceuticals Co., Ltd.) | 0.1 |
| Acerola extract ("NICHIREI ACEROLA EXTRACT WB" (tradename) available from Nichirei Bioscience Inc.) | 0.2 |
| Propylene glycol | 2.0 |
| Glycerol | 10.0 |
| Disodium edetate | 0.2 |
| Phenoxy ethanol | 0.1 |
| Dimethiconol ("YF3802A" (tradename) available from Momentive Performance Materials Inc.; 80,000 mm$^2$/s; 25° C.) | 0.5 |
| Potassium hydroxide | q.s. |
| Pigment granules (produced in Production Example 23 in which the content of the pigment component in the pigment granules was adjusted to 50%) | 0.1 |
| Perfume | q.s. |
| Purified water | balance |

Example 31 (Facial Cleanser)

The facial cleanser having the following composition was prepared by an ordinary method (pH 9/25° C.), and subjected to the same evaluation as described above. As a result, it was confirmed that the thus prepared facial cleanser was prevented from suffering from coloration of the preparation itself, and exhibited excellent properties as to all of coloration of foams upon use, impression of an appearance of the preparation when put on hands, foamability and stability. Further, the electrical conductivity of the 5-fold diluted solution obtained in Example 31 was 0.590 S/m.

| (Components) | Compounding amount (% by mass) |
|---|---|
| Lauric acid | 5.0 |
| Myristic acid | 20.0 |
| Stearic acid | 2.0 |
| Hydroxyalkyl hydroxyethyl alanine | 5.0 |
| Coconut oil fatty acid monoethanol amide | 2.0 |
| POE cetyl ether | 1.0 |
| Glycerol isostearate | 1.0 |
| Sodium coconut oil fatty acid methyl taurine | 1.0 |
| Solution of acrylamide/acrylic acid/dimethyl diallyl ammonium chloride copolymer ("MERQUAT PLUS 3330" (tradename) available from Nalco Co., Ltd.) | 1.0 |
| Ethylene glycol distearate | 1.0 |
| Glycerol | 30.0 |
| Phenoxy ethanol | 0.1 |
| *Hypericum Erectum* Extract (St. John's wort extract) ("*Hypericum Erectum* Extract" (tradename) available from Koei Kogyo Co., Ltd.) | 0.1 |
| Royal jelly extract ("Royal Jelly Extract B" (tradename) available from Ikedatohka Industries Co., Ltd.) | 0.1 |
| Brown sugar extract | 0.1 |
| Grapefruit extract ("PHARCOLEX GRAPEFRUIT B" (tradename) available from ICHIMARU PHARCOS Co., Ltd.) | 0.1 |
| *Rehmannia* root extract ("PHARCOLEX *REHMANNIA* ROOT B" (tradename) available from ICHIMARU PHARCOS Co., Ltd.) | 0.1 |
| Potassium hydroxide | q.s. |
| Pigment granules (produced in Production Example 25 in which the content of the pigment component in the pigment granules was adjusted to 78%) | 0.3 |
| Perfume | q.s. |
| Purified water | balance |

Example 32 (Facial Cleanser)

The facial cleanser having the following composition was prepared (pH 6/25° C.), and subjected to the same evaluation as described above. As a result, it was confirmed that the thus prepared facial cleanser was prevented from suffering from coloration of the preparation itself, and exhibited excellent properties as to all of coloration of foams upon use, impression of an appearance of the preparation when put on hands, foamability and stability. Further, the electrical conductivity of the 5-fold diluted solution obtained in Example 32 was 0.415 S/m.

| (Components) | Compounding amount (% by mass) |
|---|---|
| Potassium myristoyl glutamate | 6.0 |
| Potassium cocoyl glycine | 6.0 |
| PEG-400 | 15.0 |
| PEG-20 | 5.0 |
| Hydroxyalkyl hydroxyethyl alanine | 2.0 |
| Coconut oil fatty acid monoethanol amide | 1.0 |
| Hydroxypropyl cellulose | 0.2 |
| POE cetyl ether | 1.0 |
| Glycerol isostearate | 1.0 |
| Sodium coconut oil fatty acid methyl taurine | 1.0 |
| Solution of dimethyl diallyl ammonium chloride/acrylamide copolymer ("MERQUAT 550" (tradename) available from Nalco Co., Ltd.) | 1.0 |
| 1,3-Butylene glycol | 5.0 |
| Glycerol | 10.0 |
| Kaolin | 5.0 |

-continued

| (Components) | Compounding amount (% by mass) |
|---|---|
| Talc | 5.0 |
| Phenoxy ethanol | 0.1 |
| *Hypericum Erectum* Extract (St. John's wort extract) ("*Hypericum Erectum* Extract" (tradename) available from Koei Kogyo Co., Ltd.) | 0.1 |
| Royal jelly extract ("Royal Jelly Extract B" (tradename) available from Ikedatohka Industries Co., Ltd.) | 0.1 |
| Brown sugar extract ("KOKUTO OLIGOPURE III" (tradename) available from YAMAKAWA & Co., Ltd.) | 0.1 |
| Grapefruit extract ("PHARCOLEX GRAPEFRUIT B" (tradename) available from ICHIMARU PHARCOS Co., Ltd.) | 0.1 |
| Apricot juice ("APRICOT EXTRACT" (tradename) available from ELIZABETH Co., Ltd.) | 0.1 |
| Potassium hydroxide | q.s. |
| Pigment granules (produced in Production Example 26 in which the content of the pigment component in the pigment granules was adjusted to 30%) | 0.05 |
| Perfume | q.s. |
| Purified water | balance |

INDUSTRIAL APPLICABILITY

The detergent composition of the present invention is capable of not only satisfying both of rich foaming and good preparation stability, but also exhibiting a sufficient coloration of foams and readily controlling a coloring time of the foams without damage to motivation of the user to use the detergent composition, and therefore can provide a comfortable feeling of use and a suitable configuration of use according to the applications by the user.

The invention claimed is:

1. A detergent composition, comprising:
   pigment granules comprising a water-insoluble pigment (A) in the pigment granules in an amount of from 10 by mass to 95% by mass, and at least two compounds (B) selected from the group consisting of polyvinyl alcohol, a polyvinyl alcohol compound, polyvinyl pyrrolidone and a polyvinyl pyrrolidone compound,
   wherein component (B) comprises (b1) at least one compound selected from the group consisting of polyvinyl alcohol and a polyvinyl alcohol compound, each of the polyvinyl alcohol and the polyvinyl alcohol compound having a viscosity of not less than 15 mPa·s as measured with respect to a 4% aqueous solution thereof at 20° C. using a B-type viscometer, and (b2) at least one compound selected from the group consisting of polyvinyl alcohol and polyvinyl pyrrolidone, each of the polyvinyl alcohol and the polyvinyl pyrrolidone having a viscosity of less than 15 mPa·s as measured with respect to a 4% aqueous solution thereof at 20° C.

2. The detergent composition according to claim 1, wherein the water-insoluble pigment (A) are present in the pigment granules in an amount of from 18 to 80% by mass.

3. The detergent composition according to claim 1, wherein the component (B) comprises any of a combination of the polyvinyl alcohol compound (b1) and the polyvinyl alcohol (b2), a combination of the polyvinyl alcohol compound (b1) and the polyvinyl pyrrolidone (b2) and a combination of the polyvinyl alcohol (b1) and the polyvinyl pyrrolidone (b2).

4. The detergent composition according to claim 1, wherein the pigment granules are present in the detergent in an amount of from 0.001% by mass to 5% by mass.

5. The detergent composition according to claim 1, further comprising an alcohol (C) selected from the group consisting of ethanol and a polyhydric alcohol, where alcohol (C) is present in the pigment granules in an amount of not more than 5% by mass.

6. The detergent composition according to claim 1, wherein the polyvinyl alcohol compound is at least one compound selected from the group consisting of an anion-modified polyvinyl alcohol compound and a cation-modified polyvinyl alcohol compound.

7. The detergent composition according to claim 6, wherein the anion-modified polyvinyl alcohol is at least one compound selected from the group consisting of a carboxylic acid-modified polyvinyl alcohol, an undecylenic acid-modified polyvinyl alcohol and a sulfonic acid-modified polyvinyl alcohol.

8. The detergent composition according to claim 6, wherein the cation-modified polyvinyl alcohol compound is at least one compound selected from the group consisting of an ammonium-modified polyvinyl alcohol, a sulfonium-modified polyvinyl alcohol and an amino group-modified polyvinyl alcohol.

9. The detergent composition according to claim 1, wherein component (B) is present in the pigment granules in an amount of from 0.05% by mass to 50% by mass.

10. The detergent composition according to claim 1, wherein a 5-fold diluted solution prepared by diluting the detergent composition 5 times with water has an electrical conductivity of 0.1 S/m or more and 1.7 S/m or less.

11. A process for producing the detergent composition according to claim 1, comprising
    mixing and granulating a powder comprising the water-insoluble pigment (A) and a solution of the component (B) to obtain a granulated product;
    drying the resulting granulated product to obtain the pigment granules; and
    mixing the pigment granules with a detergent.

* * * * *